(12) United States Patent
Haskell-Luevano

(10) Patent No.: US 8,058,240 B2
(45) Date of Patent: Nov. 15, 2011

(54) BIOLOGICAL ACTIVE LIGANDS OF MELANOCORTIN RECEPTORS

(75) Inventor: Carrie Haskell-Luevano, Archer, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 75 days.

(21) Appl. No.: 12/296,446

(22) PCT Filed: Apr. 9, 2007

(86) PCT No.: PCT/US2007/008936
§ 371 (c)(1),
(2), (4) Date: Feb. 8, 2009

(87) PCT Pub. No.: WO2007/123839
PCT Pub. Date: Nov. 1, 2007

(65) Prior Publication Data
US 2009/0176712 A1    Jul. 9, 2009

Related U.S. Application Data

(60) Provisional application No. 60/792,703, filed on Apr. 18, 2006.

(51) Int. Cl.
*A61K 38/00* (2006.01)
(52) U.S. Cl. .................... 514/10.7; 530/317
(58) Field of Classification Search .................. None
See application file for complete search history.

(56) References Cited

U.S. PATENT DOCUMENTS

2004/0260063 A1* 12/2004 Haskell-Luevano ........ 530/350

OTHER PUBLICATIONS

Branson, R. et al., "Binge Eating as a Major Phenotype of Melanocortin 4 Receptor Gene Mutations," *N. Engl. J. Med.*, Mar. 20, 2003, vol. 348, No. 12, pp. 1096-1103.
Chai, B-X. et al, "Inverse agonist activity of agouti and agnuti-related protein," *Peptides*, 2003, vol. 24, No, 4, pp. 603-609.
Chen, W. et al., "A Calorimetric Assay for Measuring Activation of $G_s$- and $G_q$-Coupled Signaling Pathways," *Analytical Biochemistry*, Apr. 1995, vol. 226, No. 2, pp. 349-354.
Chen, W. et al., "Exocrine gland dysfunction in MC5-R-deficient mice: evidence for coordinated regulation of exocrine gland function by melanocortin peptides," *Cell*, 1997, vol. 91, pp. 789-798.
Dubern, B. et al., "Mutational analysis of melanocortin-4 receptor, agouti-related protein, and α-melanocyte-stimulating hormone genes in severely obese children," *J. Pediatr.*, Aug. 2001, vol. 139, No. 2, pp. 204-209.
Eipper, B.A. et al., "Structure and Biosynthesis of Pro-Adrenocorticotropin/Endorphin and Related Peptides," *Endocrine Reviews*, Mar. 1980, vol. 1, No. 1, pp. 1-27, Abstract only.
Fan, W. et al., "Role of melanocortinergic neurons in feeding and the *agouti* obesity syndrome," *Nature*, 1997, vol. 385, pp. 165-168.
Farooqi, I.S. et al., "Clinical spectrum of obesity and mutations in the melanocortin 4 receptor gene," *N. Engl. J. Med.*, 2003, vol. 348, No. 12, pp. 1085-1095.
Farooqi, I.S. et al., "Dominant and recessive inheritance of morbid obesity associated with melanocortin 4 receptor deficiency," *J. Clin. Invest.*, 2000, vol. 106, No. 2, pp. 271-279.
Haskell-Luevano, C. et al., "Agouti-related protein functions as an inverse agonist at a constitutively active brain melanocortin-4 receptor," *Regulatory Peptides*, 2001, vol. 99, pp. 1-7.
Haskell-Luevano, C. et al., "Structure Activity of the Melanocortin-4 Receptor in Vitro Mutagenesis: Identification of Agouti-Related Protein (AGRP), Melanocortin Agonist and Synthetic Peptide Antagonist Interaction Determinants," *Biochemistry*, Apr. 2001, vol. 40, pp. 6164-6179.
Haskell-Luevano, C. et al., "The agouti-related protein decapeptide (Yc[CRFFNAFC]Y) possesses agonist activity at the murine melanocortin-1 receptor," *Peptides*, 2000, vol. 21, pp. 683-689.
Hinney, A. et al., "Melanocortin-4 Receptor Gene: Case-Control Study and Transmission Disequilibrium Test Confirm that Functionally Relevant Mutations are Compatible with a Major Gene Effect for Extreme Obesity," *J. Clin. Endocrinol. Metab.*, Sep. 2003, vol. 88. No. 9, pp. 4258-4267.
Hinney, A. et al., "Several mutations in the melanocortin-4 receptor gene including a nonsense and a frameshift mutation associated with dominantly inherited obesity in humans," *J. Clin. Endocrinol. Metab.*, 1999, vol. 84, No. 4, pp. 1483-1486.
Hinney, A. et al., "Systematic mutation screening of the Pro-Opiomelanocortin Gene: Identification of Several Genetic Variants including three different insertions, one nonsense and two missense point mutations in probands of different weight extremes," *J. Clin. Endocrinol. Metab.*, 1998, vol. 83, No. 10, pp. 3737-3741.
Ho, G. et al., "Functional Characterization of Mutations in Melanocortin-4 Receptor Associated with Human Obesity," *J. Biol. Chem.*, Dec. 10, 1999, vol. 274, No, 50, pp. 35819-35822.
Huszar, D. et al., "Targeted disruption of the melanocortin-4 receptor results in obesity in mice," *Cell*, 1997, vol. 88, pp. 131-141.
Kask, A. et al., "Selective antagonist for the melanocortin-4 receptor (HS014) increases food intake in free-feeding rats," *Biochem. Biophys. Res. Commun.*, 1998, vol. 245, pp. 90-93.
Kiefer, L. et al., "Mutations in the carboxyl terminus of the agouti protein decrease agouti inhibition of ligand binding to the melanocortin receptors," *Biochemistry*, 1997, vol. 36, pp. 2084-2090.
Krude, H. et al., "Severe early-onset obesity, adrenal insufficiency and red hair pigmentation caused by *POMC* mutations in humans," *Nat. Genet.*, 1998, vol. 19, No. 2, pp. 155-157.

(Continued)

*Primary Examiner* — Robert Landsman
*Assistant Examiner* — Ian Dang
(74) *Attorney, Agent, or Firm* — Saliwanchik, Lloyd, Elsenschenk

(57) ABSTRACT

Disclosed are novel ligands based on an AGRP template that can rescue endogenous melanocortin agonist and/or antagonist dysfunction at MCR polymorphisms. In particular, the present invention provides novel synthetic ligands based on AGRP templates that can rescue endogenous melanocortin agonist dysfunction at MC4R polymorphisms to treat children and adults with these mutations and increase their quality of life.

2 Claims, 8 Drawing Sheets

OTHER PUBLICATIONS

Larsen, L. H. et al., "Prevalence of Mutations and Functional Analyses of Melanocortin 4 Receptor Variants Identified among 750 Men with Juvenile-Onset Obesity," *J. Clin. Endocrinol. Metab.*, 2005, vol. 90, No. 1, pp. 219-224.

Lubrano-Berthelier, C. et al., "Intracellular retention is a common characteristic of childhood obesity-associated MC4R mutations," *Human Molecular Genetics*, 2003, vol. 12, No. 2, pp. 145-153.

Nijenhuis, W.A. et al., "AgRP(83-132) acts as an inverse agonist on the human-melanocortin-4 receptor," *Mol. Endocrinol.*, 2001, vol. 15, No. 1, pp. 164-171.

Ollmann, M.M. et al., "Antagonism of Central Melanocortin Receptors in Vitro and in Vivo by Agouti-related protein," *Science*, 1997, vol. 278, pp. 135-138.

Smith, A.I. et al., "Proopiomelanocortin Processing in the Pituitary, Central Nervous System, and Peripheral Tissues," *Endocrine Reviews*, 1988, vol. 9, pp. 159-179, Abstract only.

Tota, M.R. et al., "Molecular interaction of Agouti protein and Agouti-related protein with human melanocortin receptors," *Biochemistry*, 1999, vol. 38, pp. 897-904.

Vaisse, C. et al., "Melanocortin-4 receptor mutations are a frequent and heterogeneous cause of morbid obesity," *J. Clin. Invest.*, 2000, vol. 106, No. 2, pp. 253-262.

Vaisse, C. et al., "A frameshift mutation in human *MC4R* is associated with a dominant form of obesity," *Nat Genet*, 1998, vol. 20, No. 2, pp. 113-114.

Wilczynski, A.M. et al., "Current Trends in the Structure-Activity Relationship Studies of the Endogenous Agouti-Related Protein (AGRP) Melanocortin Receptor Antagonist," *Medicinal Research Reviews*, 2005, vol. 25, No. 5, pp. 545-556.

Wilczynski, A. et al., "Identification of Putative Agouti-Related Protein(87-132)-Melanocortin-4 Receptor Interactions by Homology Molecular Modeling and Validation Using Chimeric Peptide Ligands," *J. Med. Chem.*, Mar. 20, 2004, vol. 47, No. 9, pp. 2194-2207.

Wilczynski, A. et al., "Structural Characterization and Pharmacology of a Potent (Cys101-Cys119, Cys110-Cys117) Bicyclic Agouti-Related Protein (AGRP) Melanocortin Receptor Antagonist," *J. Med. Chem.*, Oct. 2004, vol. 47, pp. 5662-5673.

Wilczynski, A. et al., "Structure-Activity Relationships of the Unique and Potent Agouti-Related Protein (AGRP)-Melanocortin Chimeric Tyr-c[β-Asp-His-DPhe-Arg-Trp-Asn-Ala-Phe-Dpr]-Tyr-NH Peptide Template," *J. Med. Chem.*, Mar. 26, 2005, vol. 48, No. 8, pp. 3060-3075.

Yang, Y. et al., "Molecular Determinants of Ligand Binding to the Human Melanocortin-4 Receptor," *Biochemistry*, Oct. 2000, vol. 39, pp. 14900-14911.

Yaswen, L. et al., "Obesity in the mouse model of pro-opiomelanocortin deficiency responds to peripheral melanocortin," *Nature Medicine*, Sep. 1999, vol. 5, No. 9, pp. 1066-1070.

Yeo, G. et al., "A frameshift mutation in *MC4R* associated with dominantly inherited human obesity," *Nature Genetics*, Oct. 1998, vol. 20, pp. 111-112.

Yeo, G. et al., "Mutations in the human melanocortin-4 receptor gene associated with severe familial obesity disrupts receptor function through multiple molecular mechanisms," *Human Molecular Genetics*, 2003, vol. 12, No. 5, pp. 561-574.

\* cited by examiner

SEQUENCE LISTING

```
<160> NUMBER OF SEQ ID NOS: 89

<210> SEQ ID NO 1
<211> LENGTH: 13
<212> TYPE: PRT
<213> ORGANISM: Artificial Sequence
<220> FEATURE:
<223> OTHER INFORMATION: Chemically synthesized melanotropin peptide:
      alpha-melanocyte stimulating hormone (alpha-MSH)
<220> FEATURE:
<221> NAME/KEY: misc_feature
<222> LOCATION: (1)..(1)
<223> OTHER INFORMATION: Xaa = Ac-Ser (acetylserine)
<220> FEATURE:
<221> NAME/KEY: misc_feature
```

```
<222> LOCATION: (13)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa = Val-NH2

<400> SEQUENCE: 1

Xaa Tyr Ser Met Glu His Phe Arg Trp Gly Lys Pro Xaa
1               5                   10

<210> SEQ ID NO 2
<211> LENGTH: 22
<212> TYPE: PRT
<213> ORGANISM: Artificial sequence
<220> FEATURE:
<223> OTHER INFORMATION: Chemically synthesized melanotropin peptide:
      beta-melanocyte stimulating hormone (beta-MSH)

<400> SEQUENCE: 2

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 3
<211> LENGTH: 12
<212> TYPE: PRT
<213> ORGANISM: Artificial Sequence
<220> FEATURE:
<223> OTHER INFORMATION: Chemically synthesized melanotropin peptide:
      gamma2-melanocyte stimulating hormone (gamma2-MSH)

<400> SEQUENCE: 3

Tyr Val Met Gly His Phe Arg Trp Asp Arg Phe Gly
1               5                   10

<210> SEQ ID NO 4
<211> LENGTH: 24
<212> TYPE: PRT
<213> ORGANISM: Artificial Sequence
<220> FEATURE:
<223> OTHER INFORMATION: Chemically synthesized melanotropin peptide:
      adrenocorticotropin hormone(1-24)

<400> SEQUENCE: 4

Ser Tyr Ser Met Glu His Phe Arg Trp Gly Lys Pro Val Gly Lys Lys
1               5                   10                  15

Arg Arg Pro Val Lys Tyr Pro Asn
            20

<210> SEQ ID NO 5
<211> LENGTH: 10
<212> TYPE: PRT
<213> ORGANISM: Homo sapiens
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (10)..(10)
<223> OTHER INFORMATION: Xaa = Tyr-NH2

<400> SEQUENCE: 5

Tyr Cys Arg Phe Phe Asn Ala Phe Cys Xaa
1               5                   10
```

```
<210> SEQ ID NO 6
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide

<400> SEQUENCE: 6

Tyr Cys Ala Ala Ala Asn Ala Phe Cys Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide

<400> SEQUENCE: 7

Tyr Cys Trp Arg Phe Asn Ala Phe Cys Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (5)..(5)
<223> OTHER INFORMATION: Xaa = DPhe

<400> SEQUENCE: 8

Tyr Cys Trp Arg Xaa Asn Ala Phe Cys Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide

<400> SEQUENCE: 9

Tyr Cys Phe Arg Trp Asn Ala Phe Cys Tyr
1               5                   10

<210> SEQ ID NO 10
<211> LENGTH: 10
<212> TYPE: PRT
<213> ORGANISM: Artificial Sequence
```

```
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (3)..(3)
<223> OTHER INFORMATION: Xaa = DPhe

<400> SEQUENCE: 10

Tyr Cys Xaa Arg Trp Asn Ala Phe Cys Tyr
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide

<400> SEQUENCE: 11

Tyr Cys His Phe Arg Trp Asn Ala Phe Cys Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 12

Tyr Cys His Xaa Arg Trp Asn Ala Phe Cys Tyr
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (1)..(1)
<223> OTHER INFORMATION: Xaa = Ac-Ser (acetylserine)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa = norleucine (Nle)
<220> FEATURE:
<221> NAME/KEY: misc_feature
<222> LOCATION: (7)..(14)
```

-continued

<223> OTHER INFORMATION: cyclization of this peptide

<400> SEQUENCE: 13

Xaa Tyr Ser Xaa Tyr Cys Arg Phe Phe Asn Ala Phe Cys Tyr Lys Pro
1               5                   10                  15
Val

<210> SEQ ID NO 14
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 14

Tyr Cys Ala Xaa Arg Trp Asn Ala Phe Cys Tyr
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide

<400> SEQUENCE: 15

Tyr Cys His Ala Arg Trp Asn Ala Phe Cys Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 16

Tyr Cys His Xaa Ala Trp Asn Ala Phe Cys Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:

```
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 17

Tyr Cys His Xaa Arg Ala Asn Ala Phe Cys Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 18

Tyr Cys Pro Xaa Arg Trp Asn Ala Phe Cys Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 19

Tyr Cys Phe Xaa Arg Trp Asn Ala Phe Cys Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (3)..(3)
<223> OTHER INFORMATION: Xaa = (rac)Atc
<220> FEATURE:
<221> NAME/KEY: misc_feature
<222> LOCATION: (4)..(4)
<223> OTHER INFORMATION: Xaa = DPhe

<400> SEQUENCE: 20
```

```
Tyr Cys Xaa Xaa Arg Trp Asn Ala Phe Cys Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide

<400> SEQUENCE: 21

Tyr Cys His Pro Arg Trp Asn Ala Phe Cys Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = (pI)DPhe

<400> SEQUENCE: 22

Tyr Cys His Xaa Arg Trp Asn Ala Phe Cys Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DNal(2')

<400> SEQUENCE: 23

Tyr Cys His Xaa Arg Trp Asn Ala Phe Cys Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
```

<223> OTHER INFORMATION: Xaa = DNal(1')

<400> SEQUENCE: 24

Tyr Cys His Xaa Arg Trp Asn Ala Phe Cys Tyr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DBip

<400> SEQUENCE: 25

Tyr Cys His Xaa Arg Trp Asn Ala Phe Cys Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 26

Tyr Cys His Xaa Pro Trp Asn Ala Phe Cys Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 27

Tyr Cys His Xaa Lys Trp Asn Ala Phe Cys Tyr
1               5                   10

<210> SEQ ID NO 28
<211> LENGTH: 11
<212> TYPE: PRT
<213> ORGANISM: Artifical Sequence
<220> FEATURE:
<221> NAME/KEY: misc_feature

```
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 28

Tyr Cys His Xaa Arg Pro Asn Ala Phe Cys Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = Nal(2')

<400> SEQUENCE: 29

Tyr Cys His Xaa Arg Xaa Asn Ala Phe Cys Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = DNal(2')

<400> SEQUENCE: 30

Tyr Cys His Xaa Arg Xaa Asn Ala Phe Cys Tyr
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
```

```
<220> FEATURE:
<221> NAME/KEY: misc_feature
<222> LOCATION: (6)..(6)
<223> OTHER INFORMATION: Xaa = Bip

<400> SEQUENCE: 31

Tyr Cys His Xaa Arg Xaa Asn Ala Phe Cys Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = Tic

<400> SEQUENCE: 32

Tyr Cys His Xaa Arg Xaa Asn Ala Phe Cys Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (9)..(9)
<223> OTHER INFORMATION: Xaa = DPhe

<400> SEQUENCE: 33

Tyr Cys His Xaa Arg Trp Asn Ala Xaa Cys Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (9)..(9)
<223> OTHER INFORMATION: Xaa = diaminoproprionic acid (Dpr)

<400> SEQUENCE: 34
```

```
Tyr Asp Ala Ala Ala Asn Ala Phe Xaa Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (9)..(9)
<223> OTHER INFORMATION: Xaa = diaminoproprionic acid (Dpr)

<400> SEQUENCE: 35

Tyr Asp Trp Arg Phe Asn Ala Phe Xaa Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (5)..(5)
<223> OTHER INFORMATION: Xaa = DPhe
<220> FEATURE:
<221> NAME/KEY: misc_feature
<222> LOCATION: (9)..(9)
<223> OTHER INFORMATION: Xaa = diaminoproprionic acid (Dpr)

<400> SEQUENCE: 36

Tyr Asp Trp Arg Xaa Asn Ala Phe Xaa Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (9)..(9)
<223> OTHER INFORMATION: Xaa = diaminoproprionic acid (Dpr)

<400> SEQUENCE: 37

Tyr Asp Phe Arg Trp Asn Ala Phe Xaa Tyr
1               5                   10

<210> SEQ ID NO 38
<211> LENGTH: 10
<212> TYPE: PRT
<213> ORGANISM: Artificial Sequence
<220> FEATURE:
```

```
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (3)..(3)
<223> OTHER INFORMATION: Xaa = DPhe
<220> FEATURE:
<221> NAME/KEY: misc_feature
<222> LOCATION: (9)..(9)
<223> OTHER INFORMATION: Xaa = diaminoproprionic acid (Dpr)

<400> SEQUENCE: 38

Tyr Asp Xaa Arg Trp Asn Ala Phe Xaa Tyr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 39

Tyr Asp His Phe Arg Trp Asn Ala Phe Xaa Tyr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 40

Tyr Asp His Xaa Arg Trp Asn Ala Phe Xaa Tyr
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (1)..(1)
<223> OTHER INFORMATION: Xaa = Ac-Ser (acetylserine)
```

```
<220> FEATURE:
<221> NAME/KEY: misc_feature
<222> LOCATION: (4)..(4)
<223> OTHER INFORMATION: Xaa = Nle
<220> FEATURE:
<221> NAME/KEY: misc_feature
<222> LOCATION: (6)..(13)
<223> OTHER INFORMATION: cyclization of this peptide
<220> FEATURE:
<221> NAME/KEY: misc_feature
<222> LOCATION: (13)..(13)
<223> OTHER INFORMATION: Xaa = diaminoproprionic acid (Dpr)

<400> SEQUENCE: 41

Xaa Tyr Ser Xaa Tyr Asp Arg Phe Phe Asn Ala Phe Xaa Tyr Lys Pro
1               5                   10                  15

Val

<210> SEQ ID NO 42
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 42

Tyr Asp Ala Xaa Arg Trp Asn Ala Phe Xaa Tyr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 43

Tyr Asp His Ala Arg Trp Asn Ala Phe Xaa Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
```

```
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 44

Tyr Asp His Xaa Ala Trp Asn Ala Phe Xaa Tyr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 45

Tyr Asp His Xaa Arg Ala Asn Ala Phe Xaa Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 46

Tyr Asp Pro Xaa Arg Trp Asn Ala Phe Xaa Tyr
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
```

```
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 47

Tyr Asp Phe Xaa Arg Trp Asn Ala Phe Xaa Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (3)..(3)
<223> OTHER INFORMATION: Xaa = (rac)Atc
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 48

Tyr Asp Xaa Xaa Arg Trp Asn Ala Phe Xaa Tyr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 49

Tyr Asp His Pro Arg Trp Asn Ala Phe Xaa Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = (pI)Dphe
```

```
-continued

<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 50

Tyr Asp His Xaa Arg Trp Asn Ala Phe Xaa Tyr
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DNal(2')
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 51

Tyr Asp His Xaa Arg Trp Asn Ala Phe Xaa Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DNal(2')
<220> FEATURE:
<221> NAME/KEY: misc_feature
<222> LOCATION: (4)..(4)
<223> OTHER INFORMATION: Xaa = DNal(1')
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 52

Tyr Asp His Xaa Arg Trp Asn Ala Phe Xaa Tyr
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
```

```
<222> LOCATION: (4)..(4)
<223> OTHER INFORMATION: Xaa = DBip
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 53

Tyr Asp His Xaa Arg Trp Asn Ala Phe Xaa Tyr
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 54

Tyr Asp His Xaa Pro Trp Asn Ala Phe Xaa Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 55

Tyr Asp His Xaa Lys Trp Asn Ala Phe Xaa Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
```

```
-continued

<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 56

Tyr Asp His Xaa Arg Pro Asn Ala Phe Xaa Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = Nal(2')
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 57

Tyr Asp His Xaa Arg Xaa Asn Ala Phe Xaa Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = DNal(2')
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 58

Tyr Asp His Xaa Arg Xaa Asn Ala Phe Xaa Tyr
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
```

```
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = Bip
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 59

Tyr Asp His Xaa Arg Xaa Asn Ala Phe Xaa Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = Tic
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 60

Tyr Asp His Xaa Arg Xaa Asn Ala Phe Xaa Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (9)..(9)
<223> OTHER INFORMATION: Xaa = DPhe
<220> FEATURE:
<221> NAME/KEY: misc_feature
<222> LOCATION: (10)..(10)
<223> OTHER INFORMATION: Xaa = diaminoproprionic acid (Dpr)

<400> SEQUENCE: 61

Tyr Asp His Xaa Arg Trp Asn Ala Xaa Xaa Tyr
1               5                   10
```

```
<210> SEQ ID NO 62
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide

<400> SEQUENCE: 62

Tyr Asp Ala Ala Ala Asn Ala Phe Lys Tyr
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide

<400> SEQUENCE: 63

Tyr Asp Trp Arg Phe Asn Ala Phe Lys Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (5)..(5)
<223> OTHER INFORMATION: Xaa = DPhe

<400> SEQUENCE: 64

Tyr Asp Trp Arg Xaa Asn Ala Phe Lys Tyr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide

<400> SEQUENCE: 65

Tyr Asp Phe Arg Trp Asn Ala Phe Lys Tyr
1               5                   10

<210> SEQ ID NO 66
<211> LENGTH: 10
<212> TYPE: PRT
```

<210> SEQ ID NO 66
<211> LENGTH: 10
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(9)
<223> OTHER INFORMATION: cyclization of this peptide
<220> FEATURE:
<221> NAME/KEY: misc_feature
<222> LOCATION: (3)..(3)
<223> OTHER INFORMATION: Xaa = DPhe

<400> SEQUENCE: 66

Tyr Asp Xaa Arg Trp Asn Ala Phe Lys Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide

<400> SEQUENCE: 67

Tyr Asp His Phe Arg Trp Asn Ala Phe Lys Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 68

Tyr Asp His Xaa Arg Trp Asn Ala Phe Lys Tyr
1               5                   10

<210> SEQ ID NO 69
<211> LENGTH: 17
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (1)..(1)
<223> OTHER INFORMATION: Xaa = Ac-Ser (acetylserine)
<220> FEATURE:
<221> NAME/KEY: misc_feature
<222> LOCATION: (4)..(4)
<223> OTHER INFORMATION: Xaa = Nle
<220> FEATURE:
<221> NAME/KEY: misc_feature
<222> LOCATION: (6)..(13)
<223> OTHER INFORMATION: cyclization of this peptide

<400> SEQUENCE: 69

```
Xaa Tyr Ser Xaa Tyr Asp Arg Phe Phe Asn Ala Phe Lys Tyr Lys Pro
1               5                   10                  15

Val
```

<210> SEQ ID NO 70
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 70

```
Tyr Asp Ala Xaa Arg Trp Asn Ala Phe Lys Tyr
1               5                   10
```

<210> SEQ ID NO 71
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide

<400> SEQUENCE: 71

```
Tyr Asp His Ala Arg Trp Asn Ala Phe Lys Tyr
1               5                   10
```

<210> SEQ ID NO 72
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 72

```
Tyr Asp His Xaa Ala Trp Asn Ala Phe Lys Tyr
1               5                   10
```

<210> SEQ ID NO 73
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide

```
<220> FEATURE:
<221> NAME/KEY: misc_feature
<222> LOCATION: (4)..(4)
<223> OTHER INFORMATION: Xaa = DPhe

<400> SEQUENCE: 73

Tyr Asp His Xaa Arg Ala Asn Ala Phe Lys Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 74

Tyr Asp Pro Xaa Arg Trp Asn Ala Phe Lys Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 75

Tyr Asp Phe Xaa Arg Trp Asn Ala Phe Lys Tyr
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (3)..(3)
<223> OTHER INFORMATION: Xaa = (rac)Atc
<220> FEATURE:
<221> NAME/KEY: misc_feature
<222> LOCATION: (4)..(4)
<223> OTHER INFORMATION: Xaa = DPhe

<400> SEQUENCE: 76

Tyr Asp Xaa Xaa Arg Trp Asn Ala Phe Lys Tyr
1               5                   10
```

```
<210> SEQ ID NO 77
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide

<400> SEQUENCE: 77

Tyr Asp His Pro Arg Trp Asn Ala Phe Lys Tyr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = (pI)DPhe

<400> SEQUENCE: 78

Tyr Asp His Xaa Arg Trp Asn Ala Phe Lys Tyr
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DNal(2')

<400> SEQUENCE: 79

Tyr Asp His Xaa Arg Trp Asn Ala Phe Lys Tyr
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DNal(1')

<400> SEQUENCE: 80
```

```
Tyr Asp His Xaa Arg Trp Asn Ala Phe Lys Tyr
1               5                   10

<210> SEQ ID NO 81
<211> LENGTH: 11
<212> TYPE: PRT
<213> ORGANISM: Artificial Sequences
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DBip

<400> SEQUENCE: 81

Tyr Asp His Xaa Arg Trp Asn Ala Phe Lys Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 82

Tyr Asp His Xaa Pro Trp Asn Ala Phe Lys Tyr
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 83

Tyr Asp His Xaa Lys Trp Asn Ala Phe Lys Tyr
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
```

```
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe

<400> SEQUENCE: 84

Tyr Asp His Xaa Arg Pro Asn Ala Phe Lys Tyr
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = Nal(2')

<400> SEQUENCE: 85

Tyr Asp His Xaa Arg Xaa Asn Ala Phe Lys Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = DNal(2')

<400> SEQUENCE: 86

Tyr Asp His Xaa Arg Xaa Asn Ala Phe Lys Tyr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
```

```
<220> FEATURE:
<221> NAME/KEY: misc_feature
<222> LOCATION: (6)..(6)
<223> OTHER INFORMATION: Xaa = Bip

<400> SEQUENCE: 87

Tyr Asp His Xaa Arg Xaa Asn Ala Phe Lys Tyr
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (6)..(6)
<223> OTHER INFORMATION: Xaa = Tic

<400> SEQUENCE: 88

Tyr Asp His Xaa Arg Xaa Asn Ala Phe Lys Tyr
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Chemically synthesized melanocortin polymorphic
      receptor (MCPR) ligand
<220> FEATURE:
<221> NAME/KEY: misc_feature
<222> LOCATION: (2)..(10)
<223> OTHER INFORMATION: cyclization of this peptide
<220> FEATURE:
<221> NAME/KEY: misc_feature
<222> LOCATION: (4)..(4)
<223> OTHER INFORMATION: Xaa = DPhe
<220> FEATURE:
<221> NAME/KEY: misc_feature
<222> LOCATION: (9)..(9)
<223> OTHER INFORMATION: Xaa = DPhe

<400> SEQUENCE: 89

Tyr Asp His Xaa Arg Trp Asn Ala Xaa Lys Tyr
1               5                   10
```

BIOLOGICAL ACTIVE LIGANDS OF MELANOCORTIN RECEPTORS

CROSS-REFERENCE TO RELATED APPLICATION

This application is a National Stage Application of International Application No. PCT/US2007/008936, filed Apr. 9, 2007; which claims the benefit of provisional patent application Ser. No. 60/792,703, filed Apr. 18, 2006, which are hereby incorporated by reference in their entirety.

GOVERNMENT SUPPORT

The subject invention was made with government support under grants awarded from the National Institutes of Health under grant numbers R01DK063974, R01DK57080, and R01DK64250. The government has certain rights in the invention.

FIELD OF THE INVENTION

The present invention relates to novel chimeric peptides and templates thereof based upon melanocortin agonist peptides and agouti related protein (AGRP) antagonist peptide, and their use as drugs to treat various diseases and conditions.

BACKGROUND OF INVENTION

Today, about two-thirds of U.S. adults are overweight or obese, according to the Centers for Disease Control and Prevention. Obesity is harmful to physical health as well as an established risk factor for a number of potentially life-threatening diseases such as atherosclerosis, hypertension, diabetes, stroke, pulmonary embolism, and cancer. Moreover, obesity can wreak havoc on an individual's mental health and can affect a person's ability to interact socially with others.

Accompanying the devastating medical consequences of this problem is the severe financial burden placed on the health care system in the United States. The estimated economic cost of obesity and its associated illnesses from medical expenses and loss of income are reported to be in excess of $68 billion per year. Because of the impact of obesity on individuals and society, much effort has been expended to find ways to treat obesity, but little success has been achieved in the long-term treatment and/or prevention of obesity.

Pro-opiomelanocortin (POMC) derived peptides are known to affect food intake. Several lines of evidence support the notion that the G-protein coupled receptors (GPCRs) of the melanocortin receptor (MCR) family, several of which are expressed in the brain, are the targets of POMC derived peptides involved in the control of food intake and metabolism. Physiologically, the melanocortin system has been recognized to participate in the regulation of feeding behavior, obesity, and energy homeostasis in rodents as well as humans (Huszar, D. et al., "Targeted disruption of the melanocortin-4 receptor results in obesity in mice," Cell, 88:131-141 (1997); Fan, W. et al., "Role of melanocortinergic neurons in feeding and the agouti obesity syndrome," Nature, 385:165-168 (1997); Krude, H. et al., "Severe early-onset obesity, adrenal insufficiency and red hair pigmentation caused by POMC mutations in humans," Nat. Genet., 19(2):155-157 (1998); Vaisse, C. et al., "Melanocortin-4 receptor mutations are a frequent and heterogeneous cause of morbid obesity," J. Clin. Invest., 106(2):253-262 (2000); and Farooqi, I. S. et al., "Clinical spectrum of obesity and mutations in the melanocortin 4 receptor gene," N. Engl. J. Med., 348(12):1085-1095 (2003)).

Five distinct MCRs have thus far been identified, and these are expressed in different tissues. MC1R was initially characterized by dominant gain of function mutations at the Extension locus, affecting coat color by controlling phaeomelanin to eumelanin conversion through control of tyrosinase. MC1R is mainly expressed in melanocytes. MC2R is expressed in the adrenal gland and represents the ACTH receptor. MC3R is expressed in the brain, gut, and placenta and may be involved in the control of food intake and thermogenesis. MC4R is uniquely expressed in the brain, and laboratory observations suggest that it is also involved in the control of food intake. See Kask A, et al., "Selective antagonist for the melanocortin-4 receptor (HS014) increases food intake in free-feeding rats," Biochem. Biophys. Res. Commun., 245:90-93 (1998)). MC5R is expressed in many tissues, including white fat, placenta and exocrine glands. MC5R knockout mice reveal reduced sebaceous gland lipid production (Chen et al., "Exocrine gland dysfunction in MC5-R-deficient mice: evidence for coordinated regulation of exocrine gland function by melanocortin peptides," Cell, 91:789-798 (1997)).

The melanotropin peptides, $\alpha$-, $\beta$- and $\gamma$-melanocyte stimulating hormone (MSH) and adrenocorticotropin hormone (ACTH), are the endogenous agonists of the melanocortin receptors that are derived by posttranslational processing of the POMC precursor hormone (see, for example, Eipper, B. A. and Mains, R. E. (1980) Endocrin. Rev., 1:1-26; and Smith, A. I. and Funder, J. W. (1988) Endocrin. Rev., 9:159-179). The endogenous melanocortin receptor antagonist, Agouti-related protein ((AGRP) is a signaling molecule involved in weight homeostasis that, when overexpressed, has been shown to cause adult onset obesity and diabetes.

AGRP is a competitive antagonist of melanocortin agonist ligands at the centrally expressed melanocortin-3 (MC3R) and melanocortin-4 (MC4R) receptors (Ollmann, M. M. et al. (1997) Science, 278:135-138). In vitro pharmacological studies have demonstrated that AGRP also possesses inverse agonist activity at the MC4R (Chai, B. X. et al., "Inverse agonist activity of agouti and agouti-related protein," Peptides, 24(4): 603-609 (2003); Haskell-Luevano, C. and Monck, E. K., "Agouti-related protein functions as an inverse agonist at a constitutively active brain melanocortin-4 receptor," Regulatory Peptides, 99:1-7 (2001); and Nijenhuis, W. A. et al., "AgRP(83-132) acts as an inverse agonist on the human-melanocortin-4 receptor," Mol. Endocrinol., 15(1): 164-171 (2001)).

All endogenous melanocortin agonists contain the putative amino acid sequence (His)/Phe-Arg-Trp, postulated to be important for melanocortin receptor molecular recognition and stimulation. Further extrapolation of the homology between the antagonist Arg-Phe-Phe motif and the endogenous melanocortin agonist conserved residues Phe-Arg-Trp, implies that the antagonist residues may be mimicking the agonist Phe-Arg-Trp interactions with the melanocortin receptors, as supported by Tota, M. R., et al., "Molecular interaction of Agouti protein and Agouti-related protein with human melanocortin receptors," Biochemistry, 38:897-904 (1999) and Haskell-Luevano, C., et al., "The agouti-related protein decapeptide (Yc[CRFFNAFC]Y) possesses agonist activity at the murine melanocortin-1 receptor," Peptides, 21:683-689 (2000).

Previous structure-activity studies of the agouti peptide identified the importance of the three amino acid motif Arg-Phe-Phe that is conserved in both agouti and AGRP (see, for example, Kiefer, L. et al., "Mutations in the carboxyl terminus of the agouti protein decrease agouti inhibition of ligand binding to the melanocortin receptors," *Biochemistry*, 36:2084-90 (1997)). These studies suggest that the conserved Arg-Phe-Phe motif found in both agouti and AGRP may be important for the antagonistic and molecular recognition properties of these two molecules at the melanocortin receptors.

Tremendous efforts are being performed in attempts to identify genetic disorders resulting in human obesity and to identify drugs that can correct for the dysfunction of these protein polymorphisms. It has been clearly demonstrated that the MC4R, POMC derived endogenous agonists, and endogenous MC4R antagonist Agouti-related protein (AGRP), when modified, result in an obese phenotype in both mice and humans (see, for example, Ollmann, M. M. et al. (1997) *Science*, 278:135-138; Huszar, D. et al. (1997) *Cell*, 88:131-141; Hinney, A. et al. (1999) *J. Clin. Endocrinol. Metab.*, 84(4):1483-1486; Yaswen, L. et al. (1999) *Nat. Med.*, 5(9):1066-1070; Yeo, G. S. et al. (1998) *Nat. Genet.*, 20(2):111-112; Vaisse, C. et al. (1998) *Nat. Genet.*, 20(2):113-114; and Hinney, A. et al. (1998) *J. Clin. Endocrinol. Metab.*, 83(10):3737-3741). For example, it has been demonstrated that targeted disruption of the MC4R gene in mice results in hyperphagia and obesity (Huszar, D. et al., "Targeted disruption of the melanocortin-4 receptor results in obesity in mice," *Cell*, 88:131-141 (1997)).

MC4R has a role in regulating energy homeostasis and obesity. In humans, more than 50 different single nucleotide polymorphisms (SNPs) of the MC4R gene have been discovered. Up to a remarkable 6% of morbidly obese adults and children studied possess single heterozygous nucleotide polymorphisms (SNPs) of the MC4R. Unfortunately, to date, very little data is available other than hypotheses regarding the structure-function relationship of MC4R to the genetic predisposition to obesity in humans. In view of the need to better understand the genetics behind obesity and its relationship with MCRs, new agents, methods, and compositions for treating or preventing obesity resulting from MC4R polymorphisms need to be identified and developed.

BRIEF SUMMARY

The subject invention provides novel melanocortin polymorphic receptor (MCPR) ligands having a template based upon melanocortin agonist or antagonist peptides, such as α-, β-, and γ-MSH and agouti related protein (AGRP), and methods for preparing such ligands. The MCPR ligands of the present invention are multifunctional and demonstrate specific bioactivity at melanocortin polymorphic receptors, in particular at polymorphic MC4R. The ligands of the subject invention have the ability to normalize endogenous receptor agonist and/or antagonist potency at polymorphic melanocortin receptors.

In one embodiment of the subject invention, amino acid residues of AGRP, or an AGRP fragment, are substituted with corresponding amino acid residues of an endogenous melanocortin receptor agonist or antagonist, where the corresponding agonist/antagonist amino acid residues are important for molecular recognition and agonist activity in interacting with melanocortin receptors.

In a preferred embodiment, MCPR ligands of the invention are prepared by substituting the AGRP(111-113) Arg-Phe-Phe residues of AGRP, or a fragment of AGRP comprising AGRP(111-113) residues, with corresponding His/Dphe-Arg-Trp amino acid residues of endogenous melanocortin receptor agonists. More preferably, AGRP(111-113) Arg-Phe-Phe residues of AGRP or a fragment thereof are substituted with corresponding amino acid residues of endogenous agonist α-MSH. The skilled artisan would readily acknowledge that the α-MSH(7-9) amino acid residues are influential in α-MSH's ability to agonize the MC4R.

In another embodiment of the invention, MCPR ligands are provided that possesses mM to sub nM agonist or antagonist potency at melanocortin receptors, in particular MC4Rs, that can resolve the functional defect at an MC4 polymorphic receptor. A preferred embodiment of the invention consists of a MCPR ligand having the following amino acid sequence: Tyr-c[Cys-His-DPhe-Arg-Trp-Asn-Ala-Phe-Cys]-Tyr-NH$_2$ (SEQ ID NO:12; also referred to herein as AMW3-130), where interaction of the AMW3-130 ligand with MC4R polymorphisms resolves endogenous melanocortin agonist dysfunction. More preferably, the AMW3-130 ligand causes an increase in endogenous melanocortin receptor agonist signaling of human MC4 polymorphic receptors (such as the following human melanocortin-4 receptors: S58C, N97D, I102S, L106P, S127L, T150I, R165Q, F165W, G252S, C271Y, and I301T).

In a related embodiment, the AGRP Arg-Phe-Phe domain (AGRP(111-113)) of the ligands of the invention can include natural and/or unnatural amino acids substituted within this domain. In a preferred embodiment, the endogenous disulfide bridge between cysteine amino acids may be substituted by asparagine and diaminopropionic acid side chains of AGRP resulting in the formation of a lactam bridge. All of these embodiments present multifunction chimeric peptides that are highly potent agonists and/or antagonists of melanocortin receptors.

MCPR ligands of the present invention can be administered to a patient in a pharmaceutical composition. The pharmaceutical composition preferably includes a therapeutically effective amount of one or more subject ligands in pharmaceutical dosage form to correct functional defects of melanocortin polymorphic receptors. Using the MCPR ligands of the present invention results in improved melanocortin receptor stimulation. According to the subject invention, pharmaceutical compositions comprising such MCPR ligands can be administered to treat children and adults with melanocortin receptor mutations to improve their quality of life.

BRIEF DESCRIPTION OF SEQUENCES

Figure 1:
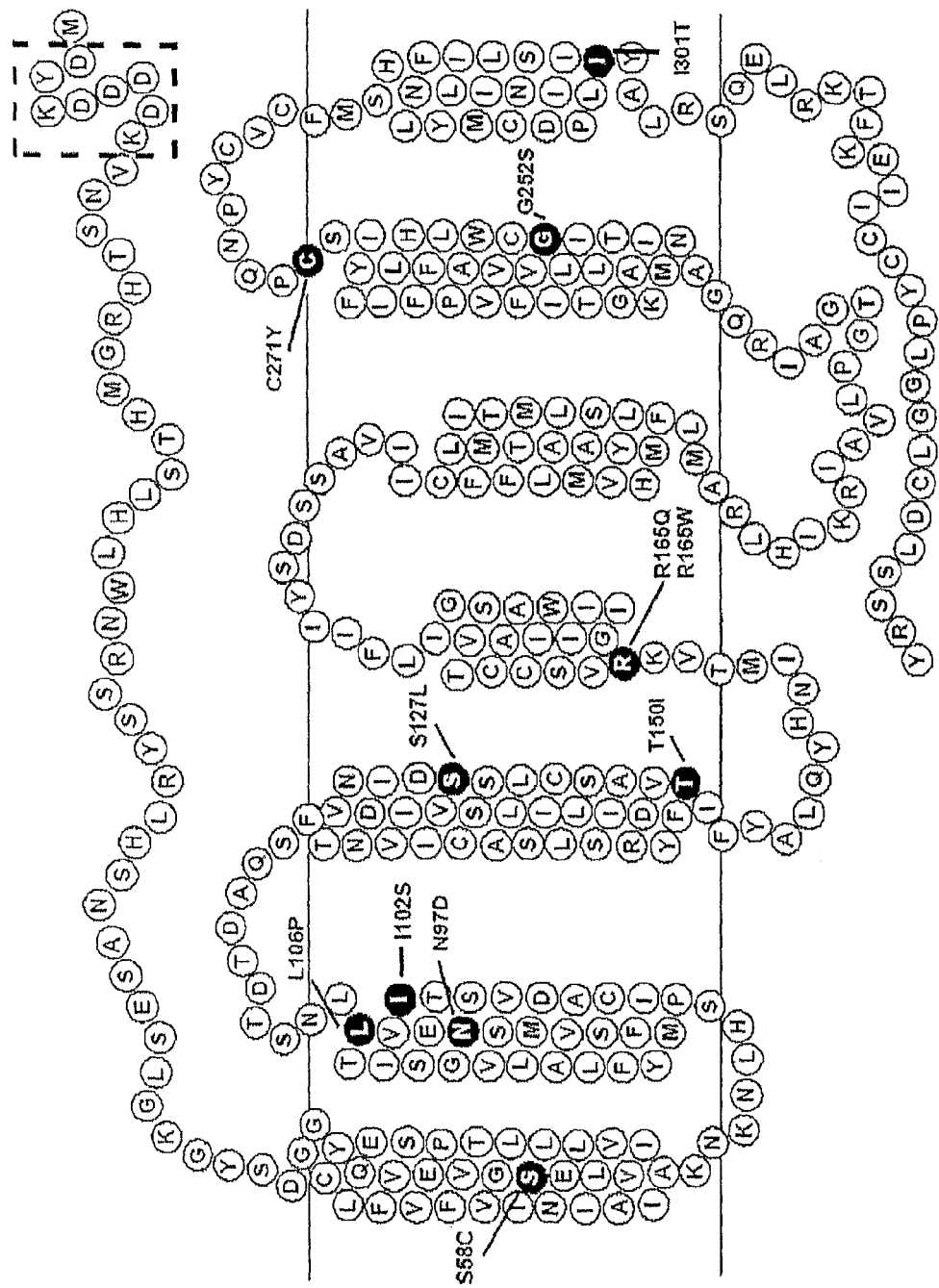
FIG. 1 is an illustration of certain human melanocortin-4 receptor polymorphisms.
Figure 2A:
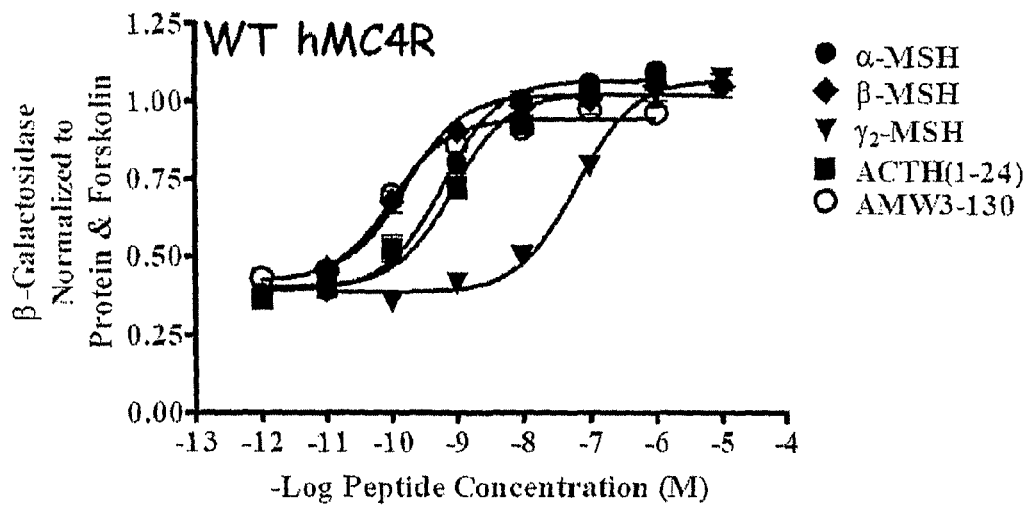
FIGS. 2A-L are graphical illustrations of the agonist pharmacology of various ligands at the human melanocortin-4 receptor polymorphisms.
Figure 2B:
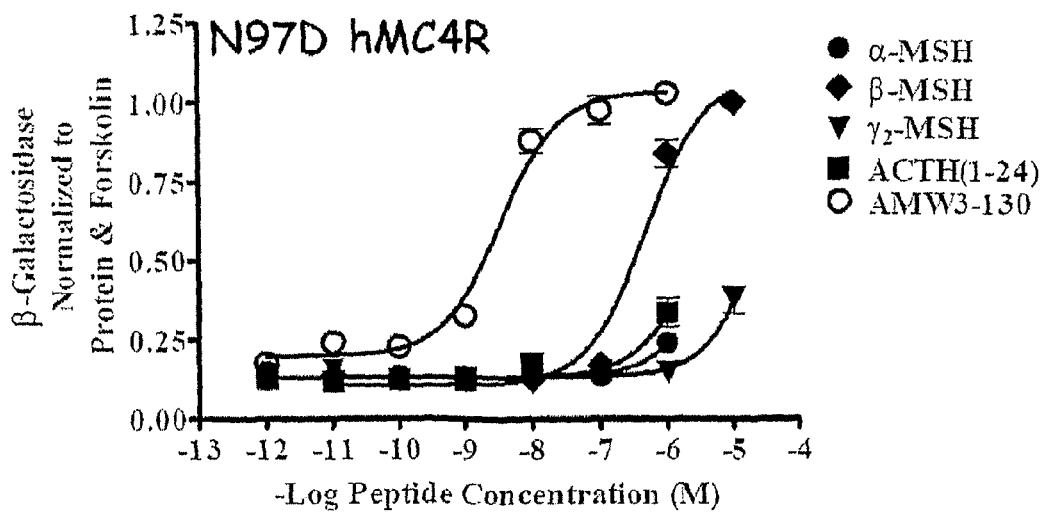
Figure 2C:
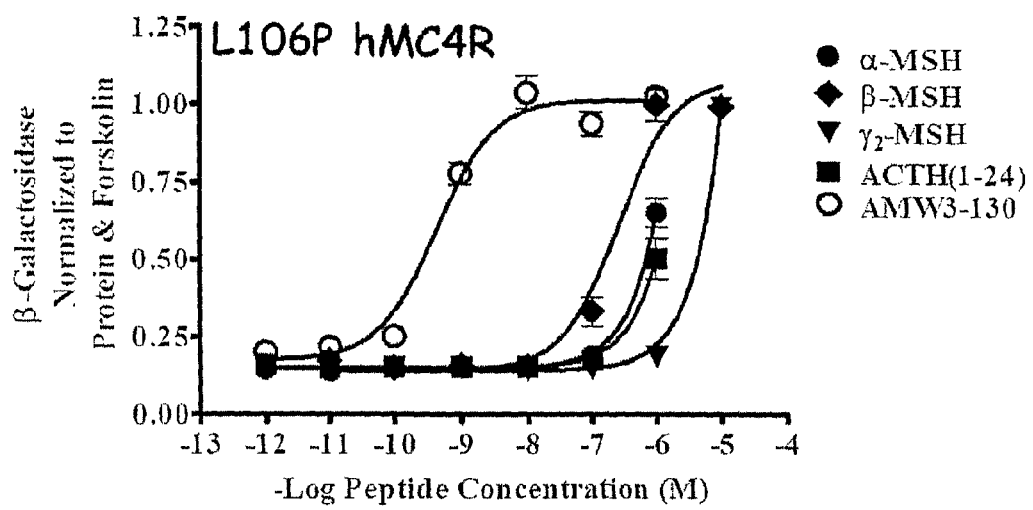
Figure 2D:
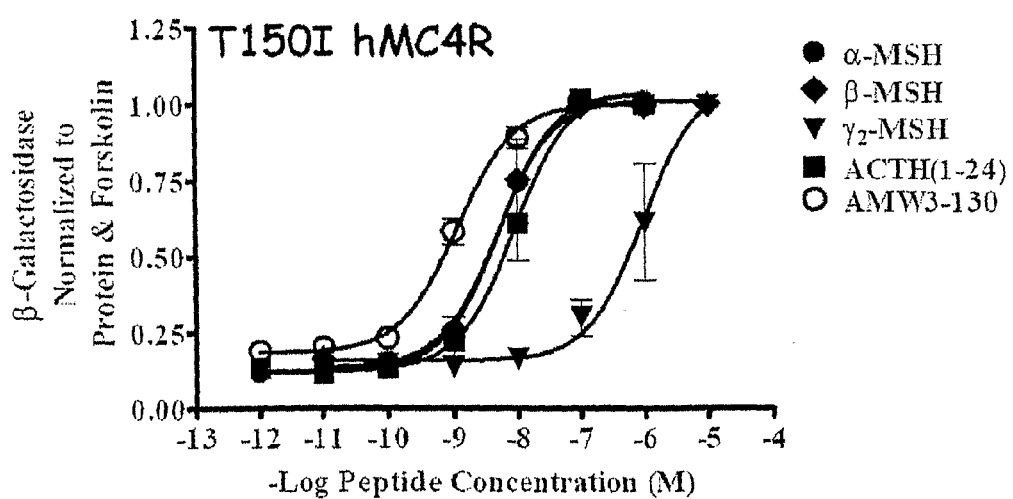
Figure 2E:
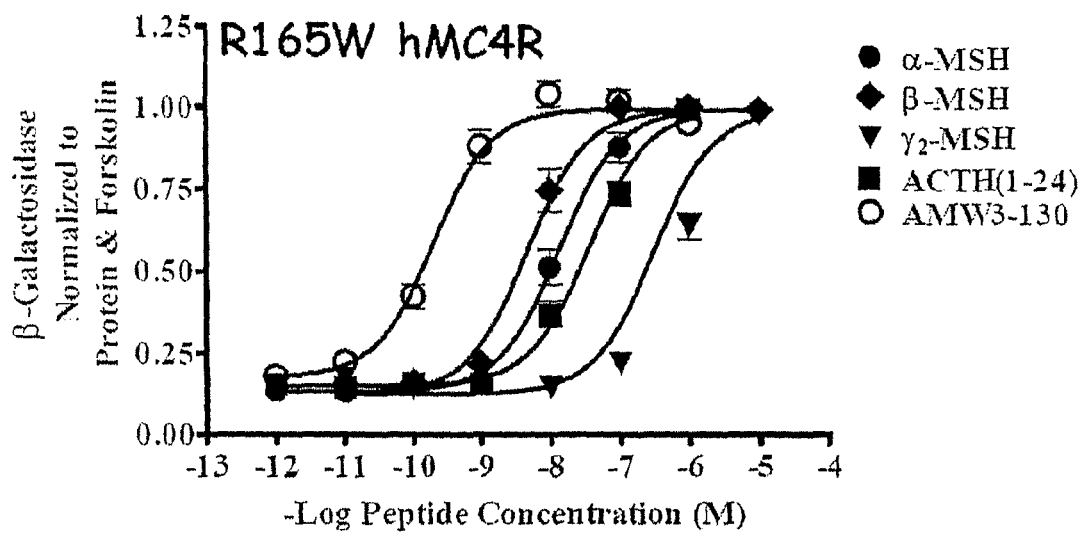
Figure 2F:
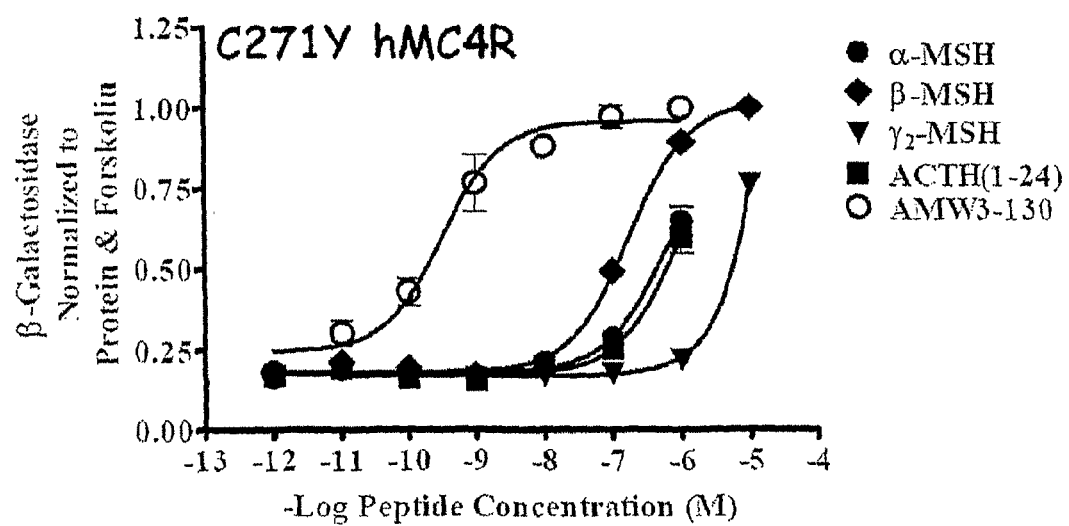
Figure 2G:
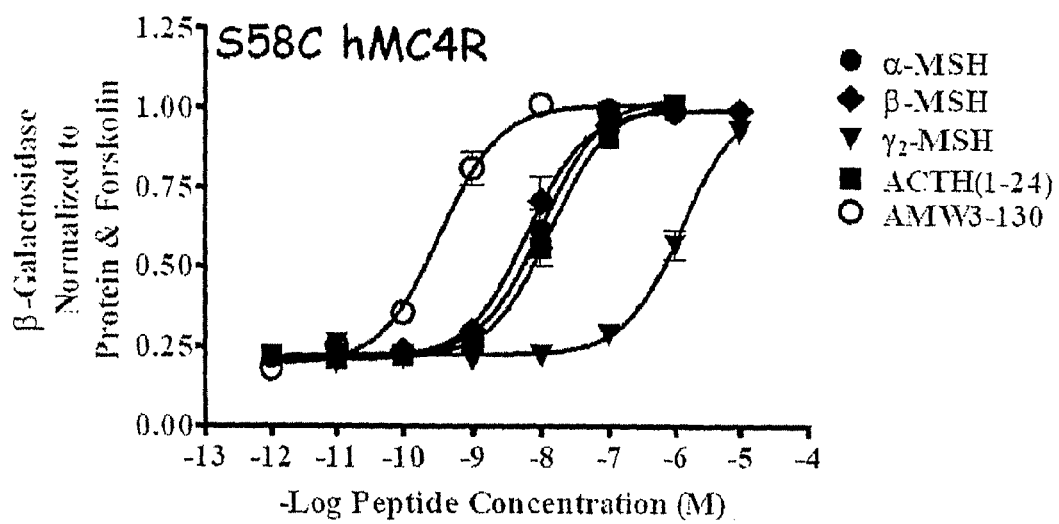
Figure 2H:
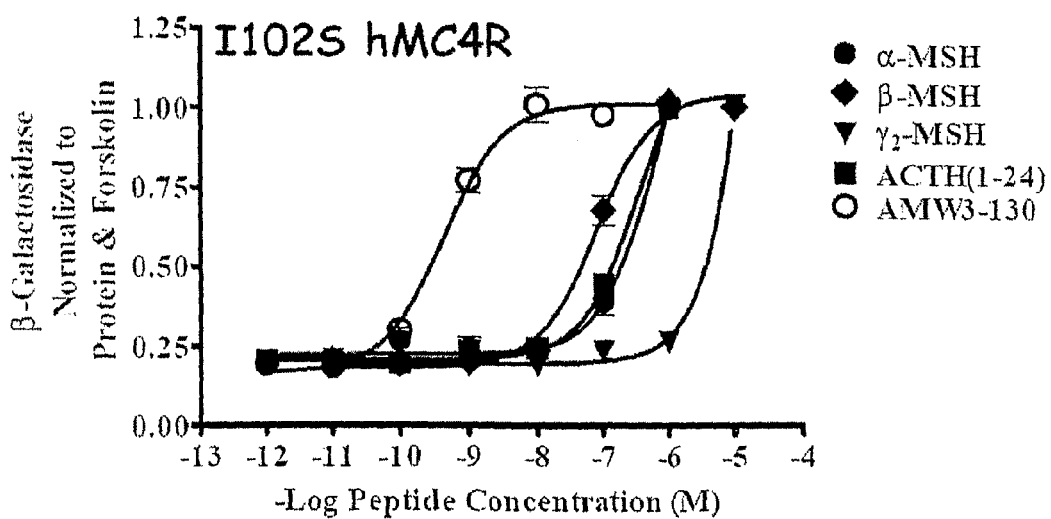
Figure 2I:
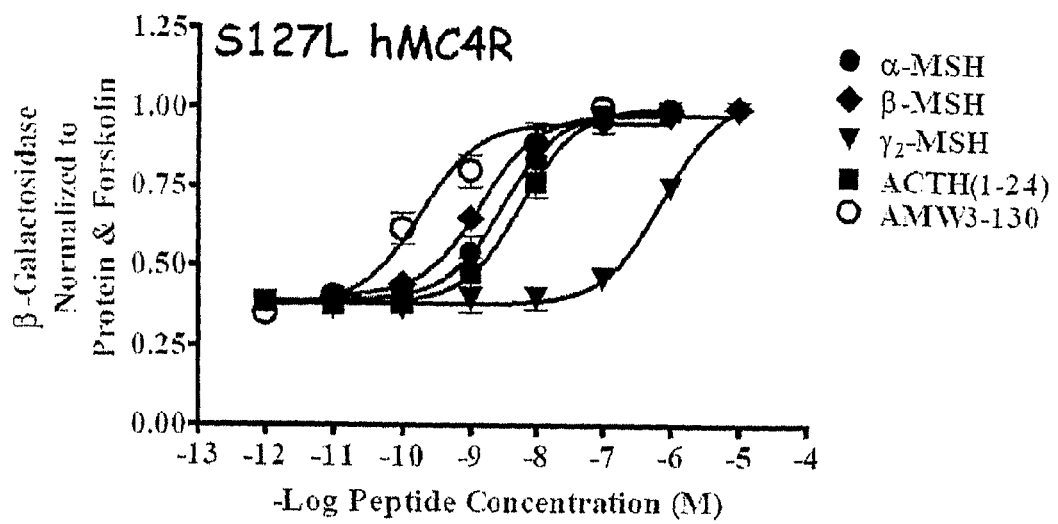
Figure 2J:
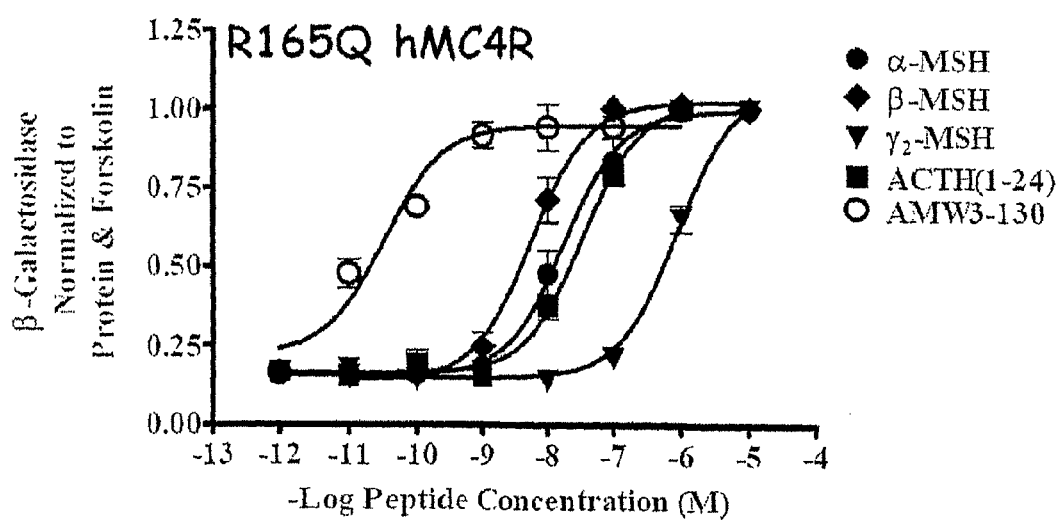
Figure 2K:
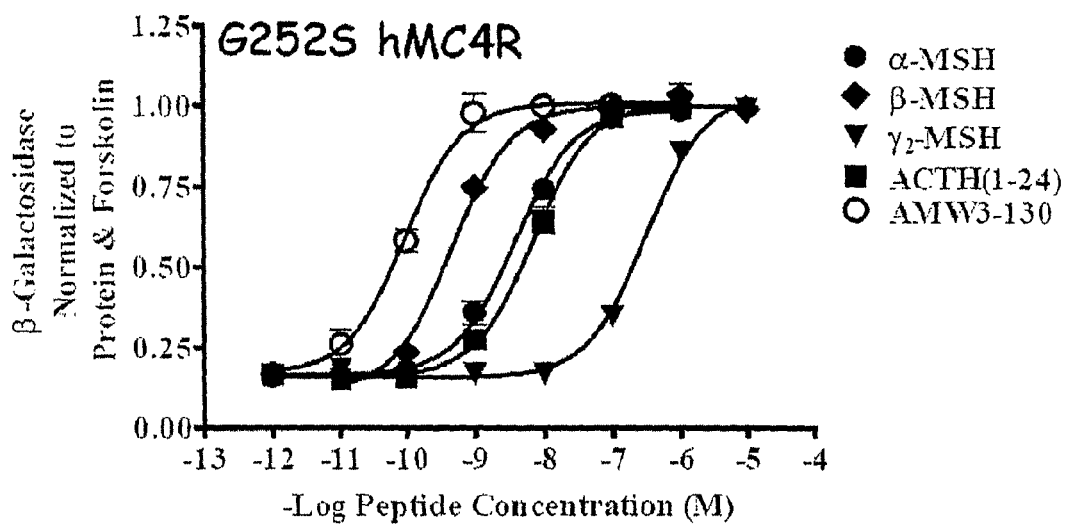
Figure 2L:
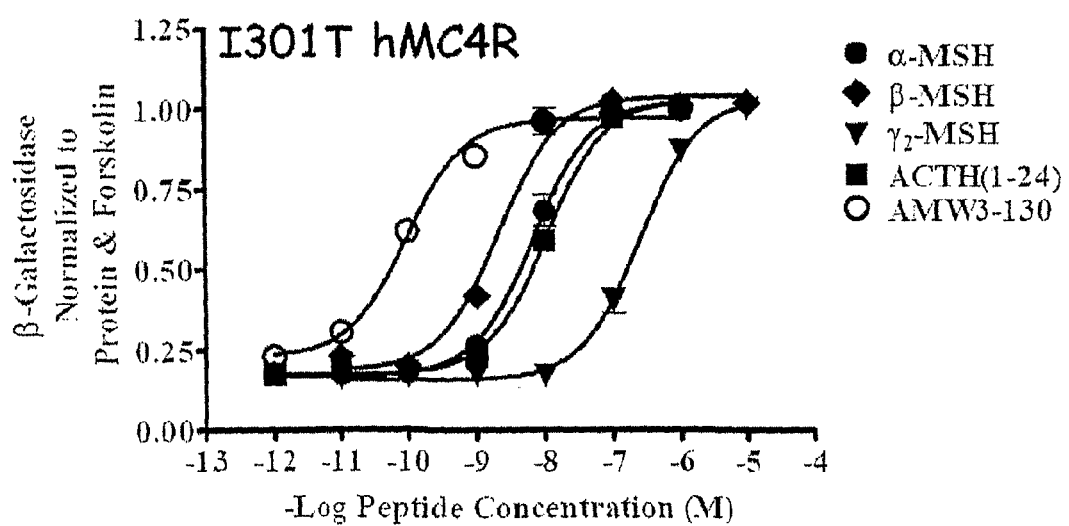

The synthesized peptides in accordance with the present invention are based either on an AGRP(109-118) template containing melanocortin based amino acid residues or on a melanocortin agonist or antagonist template containing hAGRP(111-113) Arg-Phe-Phe amino acids. For purposes of experimentation and comparison, the peptides of:

SEQ ID NO: 1 (Ac-Ser-Tyr-Ser-Met-Glu-His-Phe-Arg-Trp-Gly-Lys-Pro-Val-NH$_2$) also known as α-MSH;

SEQ ID NO:2 (Ala-Glu-Lys-Lys-Asp-Glu-Gly-Pro-Tyr-Arg-Met-Glu-His-Phe-Arg-Trp-Gly-Ser-Pro-Pro-Lys-Asp) as known as β-MSH;

SEQ ID NO:3 (Tyr-Val-Met-Gly-His-Phe-Arg-Trp-Asp-Arg-Phe-Gly) also known as γ$_2$-MSH;

SEQ ID NO:4 (Ser-Tyr-Ser-Met-Glu-His-Phe-Arg-Trp-Gly-Lys-Pro-Val-Gly-Lys-Lys-Arg-Arg-Pro-Val-Lys-Tyr-Pro-Asn) also known as ACTH(1-24); and SEQ ID NO:5 (Tyr-c[Cys-Arg-Phe-Phe-Asn-Ala-Phe-Cys]-Tyr-NH$_2$) also known as human AGRP(109-118), were either purchased from commercial sources or synthesized. Peptides of the present invention include the following (from amino to carboxy terminal):

| Sequence | SEQ ID NO |
|---|---|
| Tyr-c[Cys-Ala-Ala-Ala-Asn-Ala-Phe-Cys]-Tyr; | (SEQ ID NO: 6) |
| Tyr-c[Cys-Trp-Arg-Phe-Asn-Ala-Phe-Cys]-Tyr; | (SEQ ID NO: 7) |
| Tyr-c[Cys-Trp-Arg-DPhe-Asn-Ala-Phe-Cys]-Tyr; | (SEQ ID NO: 8) |
| Tyr-c[Cys-Phe-Arg-Trp-Asn-Ala-Phe-Cys]-Tyr; | (SEQ ID NO: 9) |
| Tyr-c[Cys-DPhe-Arg-Trp-Asn-Ala-Phe-Cys]-Tyr; | (SEQ ID NO: 10) |
| Tyr-c[Cys-His-Phe-Arg-Trp-Asn-Ala-Phe-Cys]-Tyr; | (SEQ ID NO: 11) |
| Tyr-c[Cys-His-DPhe-Arg-Trp-Asn-Ala-Phe-Cys]-Tyr; | (SEQ ID NO: 12) |
| Ac-Ser-Tyr-Ser-Nle-Tyr-c[Cys-Arg-Phe-Phe-Asn-Ala-Phe-Cys]-Tyr-Lys-Pro-Val; | (SEQ ID NO: 13) |
| Tyr-c[Cys-Ala-DPhe-Arg-Trp-Asn-Ala-Phe-Cys]-Tyr; | (SEQ ID NO: 14) |
| Tyr-c[Cys-His-Ala-Arg-Trp-Asn-Ala-Phe-Cys]-Tyr; | (SEQ ID NO: 15) |
| Tyr-c[Cys-His-DPhe-Ala-Trp-Asn-Ala-Phe-Cys]-Tyr; | (SEQ ID NO: 16) |
| Tyr-c[Cys-His-DPhe-Arg-Ala-Asn-Ala-Phe-Cys]-Tyr; | (SEQ ID NO: 17) |
| Tyr-c[Cys-Pro-DPhe-Arg-Trp-Asn-Ala-Phe-Cys]-Tyr; | (SEQ ID NO: 18) |
| Tyr-c[Cys-Phe-DPhe-Arg-Trp-Asn-Ala-Phe-Cys]-Tyr; | (SEQ ID NO: 19) |
| Tyr-c[Cys-(rac)Atc-DPhe-Arg-Trp-Asn-Ala-Phe-Cys]-Tyr; | (SEQ ID NO: 20) |
| Tyr-c[Cys-His-Pro-Arg-Trp-Asn-Ala-Phe-Cys]-Tyr; | (SEQ ID NO: 21) |
| Tyr-c[Cys-His-(pI)DPhe-Arg-Trp-Asn-Ala-Phe-Cys]-Tyr; | (SEQ ID NO: 22) |
| Tyr-c[Cys-His-DNal(2')-Arg-Trp-Asn-Ala-Phe-Cys]-Tyr; | (SEQ ID NO: 23) |
| Tyr-c[Cys-His-DNal(1')-Arg-Trp-Asn-Ala-Phe-Cys]-Tyr; | (SEQ ID NO: 24) |
| Tyr-c[Cys-His-DBip-Arg-Trp-Asn-Ala-Phe-Cys]-Tyr; | (SEQ ID NO: 25) |
| Tyr-c[Cys-His-DPhe-Pro-Trp-Asn-Ala-Phe-Cysr]-Tyr; | (SEQ ID NO: 26) |
| Tyr-c[Cys-His-DPhe-Lys-Trp-Asn-Ala-Phe-Cys]-Tyr; | (SEQ ID NO: 27) |
| Tyr-c[Cys-His-DPhe-Arg-Pro-Asn-Ala-Phe-Cys]-Tyr; | (SEQ ID NO: 28) |
| Tyr-c[Cys-His-DPhe-Arg-Nal(2')-Asn-Ala-Phe-Cys]-Tyr; | (SEQ ID NO: 29) |
| Tyr-c[Cys-His-DPhe-Arg-DNal(2')-Asn-Ala-Phe-Cys]-Tyr; | (SEQ ID NO: 30) |
| Tyr-c[Cys-His-DPhe-Arg-Bip-Asn-Ala-Phe-Cys]-Tyr; | (SEQ ID NO: 31) |
| Tyr-c[Cys-His-DPhe-Arg-Tic-Asn-Ala-Phe-Cys]-Tyr; | (SEQ ID NO: 32) |
| Tyr-c[Cys-His-DPhe-Arg-Trp-Asn-Ala-DPhe-Cys]-Tyr; | (SEQ ID NO: 33) |
| Tyr-c[Asp-Ala-Ala-Ala-Asn-Ala-Phe-Dpr]-Tyr; | (SEQ ID NO: 34) |
| Tyr-c[Asp-Trp-Arg-Phe-Asn-Ala-Phe-Dpr]-Tyr; | (SEQ ID NO: 35) |
| Tyr-c[Asp-Trp-Arg-DPhe-Asn-Ala-Phe-Dpr]-Tyr; | (SEQ ID NO: 36) |
| Tyr-c[Asp-Phe-Arg-Trp-Asn-Ala-Phe-Dpr]-Tyr; | (SEQ ID NO: 37) |
| Tyr-c[Asp-DPhe-Arg-Trp-Asn-Ala-Phe-Dpr]-Tyr; | (SEQ ID NO: 38) |
| Tyr-c[Asp-His-Phe-Arg-Trp-Asn-Ala-Phe-Dpr]-Tyr; | (SEQ ID NO: 39) |
| Tyr-c[Asp-His-DPhe-Arg-Trp-Asn-Ala-Phe-Dpr]-Tyr; | (SEQ ID NO: 40) |
| Ac-Ser-Tyr-Ser-Nle-Tyr-c[Asp-Arg-Phe-Phe-Asn-Ala-Phe-Dpr]-Tyr-Lys-Pro-Val; | (SEQ ID NO: 41) |

-continued

| | |
|---|---|
| Tyr-c[Asp-Ala-DPhe-Arg-Trp-Asn-Ala-Phe-Dpr]-Tyr; | (SEQ ID NO: 42) |
| Tyr-c[Asp-His-Ala-Arg-Trp-Asn-Ala-Phe-Dpr]-Tyr; | (SEQ ID NO: 43) |
| Tyr-c[Asp-His-DPhe-Ala-Trp-Asn-Ala-Phe-Dpr]-Tyr; | (SEQ ID NO: 44) |
| Tyr-c[Asp-His-DPhe-Arg-Ala-Asn-Ala-Phe-Dpr]-Tyr; | (SEQ ID NO: 45) |
| Tyr-c[Asp-Pro-DPhe-Arg-Trp-Asn-Ala-Phe-Dpr]-Tyr; | (SEQ ID NO: 46) |
| Tyr-c[Asp-Phe-DPhe-Arg-Trp-Asn-Ala-Phe-Dpr]-Tyr; | (SEQ ID NO: 47) |
| Tyr-c[Asp-(rac)Atc-DPhe-Arg-Trp-Asn-Ala-Phe-Dpr]-Tyr; | (SEQ ID NO: 48) |
| Tyr-c[Asp-His-Pro-Arg-Trp-Asn-Ala-Phe-Dpr]-Tyr; | (SEQ ID NO: 49) |
| Tyr-c[Asp-His-(pI)DPhe-Arg-Trp-Asn-Ala-Phe-Dpr]-Tyr; | (SEQ ID NO: 50) |
| Tyr-c[Asp-His-DNal(2')-Arg-Trp-Asn-Ala-Phe-Dpr]-Tyr; | (SEQ ID NO: 51) |
| Tyr-c[Asp-His-DNal(1')-Arg-Trp-Asn-Ala-Phe-Dpr]-Tyr; | (SEQ ID NO: 52) |
| Tyr-c[Asp-His-DBip-Arg-Trp-Asn-Ala-Phe-Dpr]-Tyr; | (SEQ ID NO: 53) |
| Tyr-c[Asp-His-DPhe-Pro-Trp-Asn-Ala-Phe-Dpr]-Tyr; | (SEQ ID NO: 54) |
| Tyr-c[Asp-His-DPhe-Lys-Trp-Asn-Ala-Phe-Dpr]-Tyr; | (SEQ ID NO: 55) |
| Tyr-c[Asp-His-DPhe-Arg-Pro-Asn-Ala-Phe-Dpr]-Tyr; | (SEQ ID NO: 56) |
| Tyr-c[Asp-His-DPhe-Arg-Nal(2')-Asn-Ala-Phe-Dpr]-Tyr; | (SEQ ID NO: 57) |
| Tyr-c[Asp-His-DPhe-Arg-DNal(2')-Asn-Ala-Phe-Dpr]-Tyr; | (SEQ ID NO: 58) |
| Tyr-c[Asp-His-DPhe-Arg-Bip-Asn-Ala-Phe-Dpr]-Tyr; | (SEQ ID NO: 59) |
| Tyr-c[Asp-His-DPhe-Arg-Tic-Asn-Ala-Phe-Dpr]-Tyr; | (SEQ ID NO: 60) |
| Tyr-c[Asp-His-DPhe-Arg-Trp-Asn-Ala-DPhe-Dpr]-Tyr; | (SEQ ID NO: 61) |
| Tyr-c[Asp-Ala-Ala-Ala-Asn-Ala-Phe-Lys]-Tyr; | (SEQ ID NO: 62) |
| Tyr-c[Asp-Trp-Arg-Phe-Asn-Ala-Phe-Lys]-Tyr; | (SEQ ID NO: 63) |
| Tyr-c[Asp-Trp-Arg-DPhe-Asn-Ala-Phe-Lys]-Tyr; | (SEQ ID NO: 64) |
| Tyr-c[Asp-Phe-Arg-Trp-Asn-Ala-Phe-Lys]-Tyr; | (SEQ ID NO: 65) |
| Tyr-c[Asp-DPhe-Arg-Trp-Asn-Ala-Phe-Lys]-Tyr; | (SEQ ID NO: 66) |
| Tyr-c[Asp-His-Phe-Arg-Trp-Asn-Ala-Phe-Lys]-Tyr; | (SEQ ID NO: 67) |
| Tyr-c[Asp-His-DPhe-Arg-Trp-Asn-Ala-Phe-Lys]-Tyr; | (SEQ ID NO: 68) |
| Ac-Ser-Tyr-Ser-Nle-Tyr-c[Asp-Arg-Phe-Phe-Asn-Ala-Phe-Lys]-Tyr-Lys-Pro-Val; | (SEQ ID NO: 69) |
| Tyr-c[Asp-Ala-DPhe-Arg-Trp-Asn-Ala-Phe-Lys]-Tyr; | (SEQ ID NO: 70) |
| Tyr-c[Asp-His-Ala-Arg-Trp-Asn-Ala-Phe-Lys]-Tyr; | (SEQ ID NO: 71) |
| Tyr-c[Asp-His-DPhe-Ala-Trp-Asn-Ala-Phe-Lys]-Tyr; | (SEQ ID NO: 72) |
| Tyr-c[Asp-His-DPhe-Arg-Ala-Asn-Ala-Phe-Lys]-Tyr; | (SEQ ID NO: 73) |
| Tyr-c[Asp-Pro-DPhe-Arg-Trp-Asn-Ala-Phe-Lys]-Tyr; | (SEQ ID NO: 74) |
| Tyr-c[Asp-Phe-DPhe-Arg-Trp-Asn-Ala-Phe-Lys]-Tyr; | (SEQ ID NO: 75) |
| Tyr-c[Asp-(rac)Atc-DPhe-Arg-Trp-Asn-Ala-Phe-Lys]-Tyr; | (SEQ ID NO: 76) |
| Tyr-c[Asp-His-Pro-Arg-Trp-Asn-Ala-Phe-Lys]-Tyr; | (SEQ ID NO: 77) |
| Tyr-c[Asp-His-(pI)DPhe-Arg-Trp-Asn-Ala-Phe-Lys]-Tyr; | (SEQ ID NO: 78) |
| Tyr-c[Asp-His-DNal(2')-Arg-Trp-Asn-Ala-Phe-Lys]-Tyr; | (SEQ ID NO: 79) |
| Tyr-c[Asp-His-DNal(1')-Arg-Trp-Asn-Ala-Phe-Lys]-Tyr; | (SEQ ID NO: 80) |
| Tyr-c[Asp-His-DBip-Arg-Trp-Asn-Ala-Phe-Lys]-Tyr; | (SEQ ID NO: 81) |

```
                                   -continued
Tyr-c[Asp-His-DPhe-Pro-Trp-Asn-Ala-Phe-Lys]-Tyr;           (SEQ ID NO: 82)

Tyr-c[Asp-His-DPhe-Lys-Trp-Asn-Ala-Phe-Lys]-Tyr;           (SEQ ID NO: 83)

Tyr-c[Asp-His-DPhe-Arg-Pro-Asn-Ala-Phe-Lys]-Tyr;           (SEQ ID NO: 84)

Tyr-c[Asp-His-DPhe-Arg-Nal(2')-Asn-Ala-Phe-Lys]-Tyr;       (SEQ ID NO: 85)

Tyr-c[Asp-His-DPhe-Arg-DNal(2')-Asn-Ala-Phe-Lys]-Tyr;      (SEQ ID NO: 86)

Tyr-c[Asp-His-DPhe-Arg-Bip-Asn-Ala-Phe-Lys]-Tyr;           (SEQ ID NO: 87)

Tyr-c[Asp-His-DPhe-Arg-Tic-Asn-Ala-Phe-Lys]-Tyr;           (SEQ ID NO: 88)
and

Tyr-c[Asp-His-DPhe-Arg-Trp-Asn-Ala-DPhe-Lys]-Tyr.          (SEQ ID NO: 89)
```

Detailed Disclosure

The present invention pertains to novel melanocortin polymorphic receptor (MCPR) ligands that are biologically active at melanocortin receptors, particularly melanocortin polymorphic receptors. The MCPR ligands of the present invention are based on the identification of AGRP and melanocortin agonist/antagonist domains involved in binding to melanocortin receptors. The invention provides novel, efficacious MCPR ligands with molecular structures that duplicate or mimic the binding domains of either AGRP or a melanocortin agonist/antagonist, where the subject ligands demonstrate the ability to stimulate MC4 polymorphic receptors.

In one embodiment, the MCPR ligands of the present invention are based on an AGRP template. The AGRP template can be the full length AGRP peptide or a region thereof. Preferably, the AGRP template consists of a region of AGRP that includes the AGRP(111-113) residues. More preferably, the AGRP template consists of the AGRP(87-132) region. Even more preferably, the AGRP template consists of the AGRP(109-118) region.

The MCPR ligands of the invention containing the AGRP template have the residues of AGRP(111-113) substituted with analogous melanocortin agonist-based bioactive determinant sequences. Alternatively, ligands containing the AGRP template have the residues of AGRP(111-113) substituted with analogous melanocortin antagonist-based bioactive determinant sequences. In related embodiments, the AGRP-based bioactive sequences (AGRP(111-113)) are substituted with natural and/or unnatural amino acids. The ligands of the present invention can have either a disulfide link (see SEQ ID NOS: 6-33) or a lactam bridge (see SEQ ID NOS:34-61); or modified bridge (see SEQ ID NOS:62-89).

Definitions

The term "patient," describes an animal, including mammals, to whom treatment with the compositions according to the present invention are provided. Mammalian species that benefit from the disclosed methods of treatment include, and are not limited to, apes, chimpanzees, orangutans, humans, monkeys; domesticated animals (e.g., pets) such as dogs, cats, guinea pigs, hamsters, rabbits, rats, mice, and ferrets; and domesticated farm animals such as cows, horses, swine, and sheep.

Figure 3:
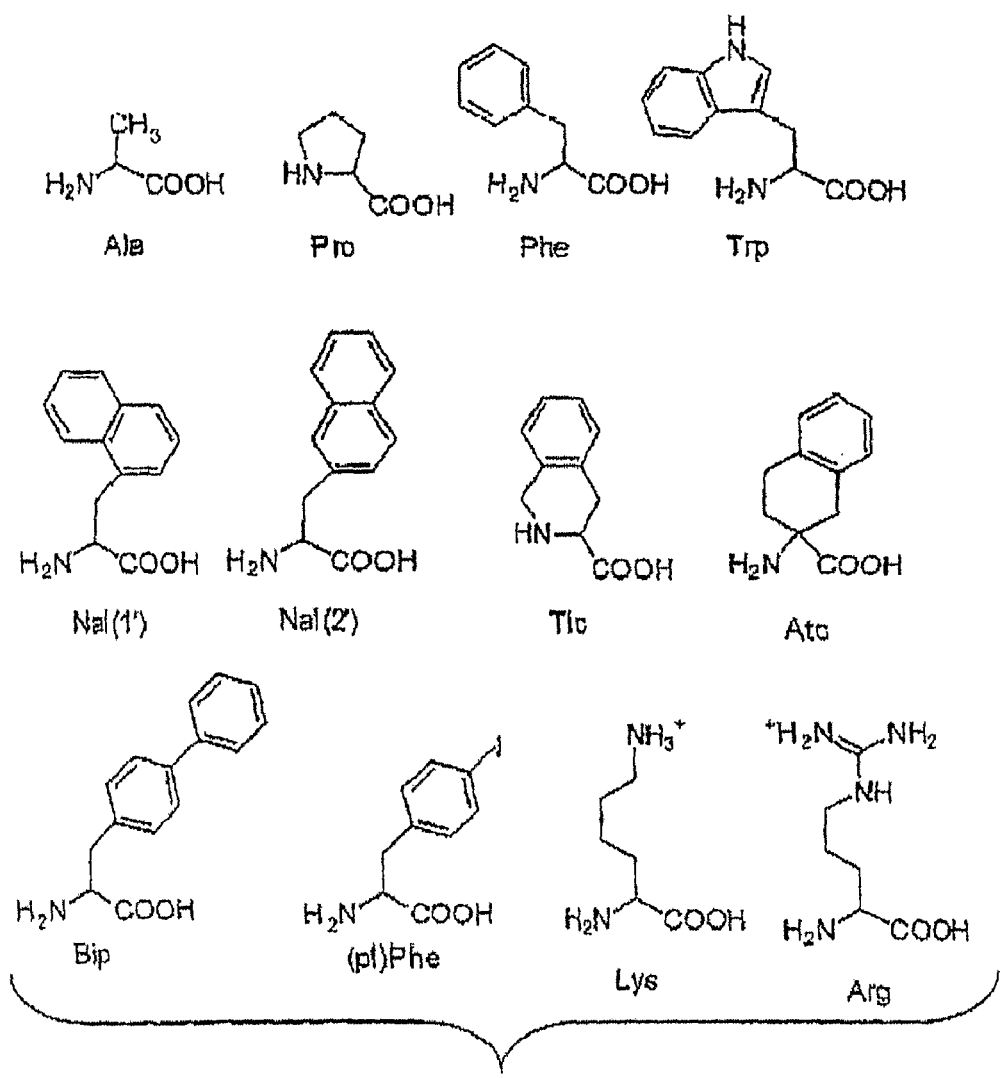
FIG. 3 provides illustrations of amino acids and their abbreviations as described herein.

In general, unless otherwise specified, the abbreviations used for the designation of amino acids and the protective groups used therefore are based on recommendations of the IUPAC-IUB Commission of Biochemical Nomenclature (*Biochemistry*, 11:1726-1732 (1972)). The nomenclature used to define compounds of the invention is that specified by IUPAC, published in *European Journal of Biochemistry*, 138: 9-37 (1984). With regard to certain amino acids disclosed herein, their structures and abbreviations are provided in FIG. 3.

The letter "D" preceding any three-letter abbreviation for an amino acid, e.g. as in "D-Nal" or "D-Phe," denotes the D-form of the amino acid. The letter "L" preceding an amino acid three-letter abbreviation denotes the natural L-form of the amino acid. For purposes of this disclosure, unless otherwise indicated, absence of a "D" or "L" designation indicates that the abbreviation refers to both the D- and L-forms. Where the common single-letter abbreviation is used, capitalization refers to the L-form and small letter designation refers to the D-form, unless otherwise indicated.

For each amino acid, an additional conservative substitution includes the "homolog" of that amino acid, where the "homolog" is an amino acid with a methylene group ($CH_2$) inserted into the side chain at the beta position of that side chain. Examples of such homologs include, without limitation, homophenylalanine, homoarginine, homoserine, and the like.

As used herein, the term "peptide," is defined as an amino acid sequence from three amino acids to about 700 amino acids in length.

As used herein, "MCPR ligand" and "ligand" refer to a compound with affinity for melanocortin polymorphic receptors, particularly melanocortin-4 polymorphic receptors, that results in measurable biological activity in cells, tissues, or organisms that contain the MC receptor or blocks stimulation by a known MC agonist. A preferred MCPR ligand of the invention has the amino acid sequence of SEQ ID NO:12. Assays that demonstrate melanocortin polymorphic receptor agonistic or antagonist activity of compounds are well known in the art.

The term "AGRP template" refers to peptides having the core amino acid sequence of AGRP(111-113) Arg-Phe-Phe, including all related peptides described herein. In one embodiment, the AGRP template includes human AGRP(87-132) residues. Preferably, the AGRP template of the invention includes the amino acid sequence of SEQ ID NO:5. The AGRP template may or may not have amino terminal methionines, depending on the manner in which they are prepared.

Related peptides includes allelic variants; fragments; derivatives; substitution, deletion, and insertion variants; fusion polypeptides; and orthologs; and each amino acid of each such related peptide may be either natural or unnatural of the "D" (natural) or "L" (unnatural) configuration which corresponds to the stereochemical designation "S" and "R," respectively, as defined in the RS system of Cahn et al., (*Pure*

Applied Chemistry, 45:11-30 (1974), and references cited therein). Such related peptides may be mature peptides, i.e., lacking a signal peptide.

As used herein, the term "MCPR ligand variants" refers to MCPR ligands of the invention whose amino acid sequences contain one or more amino acid sequence substitutions, deletions, and/or additions as compared to the MCPR ligand amino acid sequences set forth herein (such as SEQ ID NO:12). Such peptide variants containing amino acids of the natural L-configuration can be prepared from the corresponding nucleic acid molecule variants. Alternatively, such variants containing amino acids of the D-configuration (unnatural form) can be prepared synthetically using standard methods described herein (see also *Biochem. J.*, 219:345-373 (1984)).

The term "MCPR ligand derivatives," as used herein, refers to peptides, variants or fragments thereof, that have been chemically modified, as for example, by addition of one or more water soluble polymers, N-linked or O-linked carbohydrates, sugars, phosphates, and/or other such molecules, where the molecule or molecules are not naturally attached to the MCPR ligands as set forth herein (such as SEQ ID NO:12). Derivatives further include deletion of one or more chemical groups naturally attached to any of the MCPR ligands as set forth herein.

As used herein, the term "MCPR ligand nucleic acid molecule," when used to describe a nucleic acid molecule, refers to a nucleic acid molecule or fragment thereof that encodes any of the MCPR ligands as set forth herein (such as SEQ ID NO:12), and any fragments, derivatives, substitution, deletion, and insertion variants, fusion peptides, fusion polypeptides, and orthologs thereof.

The term "biological activity" or "biologically active," as used herein refers to MCPR ligands that generate a functional (agonist and/or antagonist) pharmacological response at the melanocortin polymorphic receptors.

As used herein, "measurable" means the biological activity is both reproducible and significantly different from the baseline variability of the assay.

A "pharmaceutically-acceptable salt" is a cationic salt formed at any acidic (carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like. Clearly contemplated in such salts are addition salts that may provide an optical center where once there is none. For example, a chiral tartrate salt may be prepared from the compounds of the invention, and this definition includes such chiral salts.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

Abbreviations

The abbreviation "Boc" as used herein refers to tert-butyloxycarbonyl.

The abbreviation "DCM" as used herein refers to dichloromethane.

The abbreviation "Dde" as used herein refers to (1-(4,4-dimethyl-2,6-dioxocyclohex-1-ylidene)ethyl).

The abbreviation "DIPEA" as used herein refers to diisopropylethylamine.

The abbreviation "DMF" as used herein refers to dimethylformamide.

The abbreviation "DMSO" as used herein refers to dimethyl sulphoxide.

The abbreviation "EtOAc" as used herein refers to MeOH/ethyl acetate.

The abbreviation "Fmoc" as used herein refers to 9-fluorenylmethyloxycarbonyl.

The abbreviation "HOBt" as used herein refers to N-hydroxy-benzotriazole.

The abbreviation "MBHA" as used herein refers to methylbenzydryl-amine.

The abbreviation "PyBOP" as used herein refers to benzotriazole-1-yl-oxy-tris-pyrrolidino-phosphonium hexafluorophosphate.

The abbreviation "SPPS" as used herein refers to solid-phase peptide synthesis.

The abbreviation "tBu" as used herein refers to a tert-butyl group.

The abbreviation "TFA" as used herein refers to trifluoroacetic acid.

The abbreviation "TRH" as used herein refers to thyrotropin-releasing hormone.

MCPR Ligands

The MCPR ligands of the present invention are melanocortin receptor ligands, preferably polymorphic melanocortin receptor ligands, even more preferably polymorphic melanocortin-4 receptor ligands. In one embodiment, the ligands of the invention are peptides comprising the sequence of SEQ ID NO: 12 (AMW3-130).

With reference to the peptide of SEQ ID NO:12, it is seen that the peptide comprises an important template based on AGRP(109-118), where the AGRP(111-113) Arg-Phe-Phe residues are substituted. Preferably, the Arg-Phe-Phe residues are substituted with corresponding core tri- or tetra-peptides of endogenous melanotropin peptides, where the core peptides are important for molecular recognition and bioactivity in interacting with melanocortin receptors. In a preferred embodiment, the ligands of the invention comprise an AGRP (109-118) template, where the AGRP(111-113) residues are substituted with His/Dphe-Arg-Trp amino acid residues.

That the MCPR ligands of the present invention have the ability to normalize polymorphic melanocortin receptor activity in the presence of endogenous melanotropin peptides is surprising. In the case of the ligand of SEQ ID NO: 12, given the ligand is based on an AGRP template that is a MC4R antagonist, it is even more surprising that the ligand is able to normalize endogenous melanotropin agonist potency while significantly reducing antagonist potency at polymorphic MC4Rs. One would have predicted that the ligands of the invention would lack the ability to stimulate polymorphic melanocortin receptors, let alone normalize endogenous melanotropin peptide agonist/antagonist potency at polymorphic melanocortin receptors. Surprisingly, this is not the case, as ligands of the invention exhibit the ability to interact with polymorphic melanocortin receptors to normalize endogenous melanotropin peptide potency.

Synthesis of MCPR Ligands

The MCPR ligands of the invention can be prepared using a variety of procedures. The starting materials used in preparing the ligands of the invention are known, made by known methods, or are commercially available. A general reaction for making the ligands of the invention is set forth below.

Representative examples for synthesizing representative compounds of the present invention are disclosed in the Example.

MCPR Ligand Synthesis: According to one general scheme, the claimed ligands are synthesized using standard Fmoc (9-Fluorenylmethoxycarbonyl as protection group for alpha $NH_2$) chemistry followed by deprotection, solution phase cyclization, and detailed characterization and purification. All the amino acids, reagents, and resins used for ligand synthesis can be purchased from commercial sources (such as Peptides Internation; Louisville, Ky.). The general Fmoc chemistry protocol for SPPS (solid phase peptide synthesis) includes: 1) cleavage of the Fmoc protection groups with piperidine; 2) activation of the carboxyl group of amino acids; 3) coupling of the activated amino acids to the amino-terminal of the resin bound peptide chain to form peptide bonds; and 4) repeat step 3 until the ligand synthesis is complete. Ligand synthesis can be performed on Fmoc resin using a manual synthesis reaction vessel. After the completed synthesis, the ligands are cleaved from the resin and deprotected.

Nα-Fmoc protected amino acids, such as Cys(Trt), Tyr (tBu), Arg(Pbf), His(Trt), Dphe, Phe, Asn(Trt), Trp(Boc), and Ala, can be utilized to synthesize ligands of the invention. Benzotriazol-1-yl-oxy-tris(dimethyloamino) phosphonium hexafluoro-phosphate (BOP) and 1-hydroxybenzotriazole. (HOBt) can be used as coupling reagents. Dicholoromethane (DCM), glacial acetic acid, methanol, acetonitrile, anhydrous ethyl ether, N,N-Dimethylformamide (DMF), Trifluoroacetic acid (TFA), dimethyl sulfoxide (DMSO), piperidine, phenol, N,N-diisopropylethylamine (DIEA), triisopropylsilane (TIS) and 1,2-ethanedithiol (EDT) can be used as reagents or solvents in the ligand syntheses. All reagents and chemicals used in ligand synthesis are preferably ACS grade or better and can be used without further purification.

Deprotection: The resins containing synthesized peptides are unloaded from the synthesis reaction vessel. Using a cleavage cocktail (trifluoroacetic acid (TFA), $H_2O$, EDT, phenol, and TIS) at room temperature, the MCPR ligands are cleaved off the resin and at the same time, the side chain protection groups are removed under the deprotection condition. The cleavage solution is separated from the resin, concentrated, precipitated, and purified.

Solution Phase cyclization: The MCPR ligand is characterized by reversed phase high performance liquid chromatography (RP-HPLC) and/or mass spectrometry (MS) prior to cyclization process. The purified linear ligand is oxidized to the disulfide form by reaction with 5% DMSO in $H_2O$. The ligand was dissolved at a concentration of 0.37 mg/mL and the solution was allowed to react at 20° C. Analytical RP-HPLC and/or electrospray MS is used to monitor the cyclization reaction. An HPLC system with a Vadyc column was used to assess the purity of the synthesized ligands.

A variety of additional MCPR ligands can be generated using the guidance of the scheme above.

For example, the following method can be used to prepare MCPR ligands of the invention that include a lactam bridge (see SEQ ID NOS:34-61) or modified bridge (see SEQ ID NOS:62-89). Such MCPR ligands are synthesized using standard Boc methodology on an automated synthesizer (Advanced ChemTech 440MOS, Louisville, Ky.).

The amino acids Boc-Asp(OFm), Boc-Tyr(2,6-dichloro-Bzl), Boc-His(3-Bom), Boc-DPhe, Boc-Trp(For), Boc-Asn, Boc-Ala, Boc-Phe, Boc-Pro, Boc-(2-Naphthyl)-alanine [Nal (2')], Boc-(1-Naphthyl)-D-alanine [DNal(1')], Boc-Lys(2-chloro-Z), and Boc-(2-Naphthyl)-D-alanine [DNal(2')] were purchased from Bachem (Torrance, Calif.). The Boc-Arg (Tos) and Boc-diaminopropionic (Dpr) amino acids were purchased from Peptides International (Louisville, Ky.). The amino acids Boc-para-iodo-D-phenylalanine [(pI)DPhe], Boc-4-Phenyl-D-phenylalanine (DBip), Boc-4-Phenyl-phenylalanine (Bip), and Boc-1,2,3,4-tetrahydro-3-isoquinoline carboxylic acid (Tic) were purchased from Synthetech (Albany, Oreg.). The racemic amino acid 2-N-Boc-amino-tetrahydro-2-napthyl carboxylic acid (Atc) was purchased from Pharmacore (High Point, N.C.). Para-Methyl-Benzhydrylamine Resin (p-MBHA Resin, 0.28 meq/g substitution) was purchased from Peptides International. The coupling reagents: benzotriazol-1-yl-N-oxy-tris(dimethylamino) phosphonium hexafluorophosphate (BOP), and 1-hydroxybenzotriazole (HOBt) were obtained from Peptides International. Glacial acetic acid (HOAc), dichloromethane (DCM), methanol (MeOH), acetonitrile (ACN), and anhydrous ethyl ether were purchased from Fisher (Fair Lawn, N.J., USA). N,N-dimethylformamide (DMF) was purchased from Burdick and Jackson (McGaw Park, Ill., USA). Trifluoroacetic acid (TFA), 1,3-diisopropylcarbodiimide (DIC), piperidine, were purchased from Sigma (St. Louis, Mo., USA). N-N-Diisopropylethylamine (DIEA) was purchased from Aldrich (Milwaukee, Wis., USA). All reagents and chemicals were ACS grade or better and were used without further purification.

The syntheses are performed using a 40 well Teflon reaction block with a coarse Teflon frit. Approximately 200 mg resin (0.08 mmole) is added to each reaction block well. The resin is allowed to swell for 2 hrs in 5 mL DMF and deprotected using 4 mL 50% TFA, 2% anisole in DCM for 3 min followed by a 20 min incubation at 500 rpms and washed with DCM (4.5 mL, 2 min, 500 rpms 3 times). The peptide-resin salt is neutralized by the addition of 4 mL 10% DIEA in DCM (3 min, 500 rpms, 2 times) followed by a DCM wash (4.5 mL, 2 min, 500 rpms 4 times). A positive Kaiser test result indicated free amine groups on the resin.

The growing peptide chain is added to the amide-resin using the general amino acid cycle as follows: 500 μL DMF is added to each reaction well to "wet the frit," 3-fold excess amino acid starting from the C-terminus is added [400 μM of 0.5M solution in 0.5M HOBt and BOP in DMF] followed by the addition of 400 μL 0.5M DIC in DMF and the reaction well volume is brought up to 3 mL using DMF. The coupling reaction is mixed for 1 hr at 500 rpms, followed by emptying of the reaction block by positive nitrogen gas pressure. A second coupling reaction is performed by the addition of 500 μL DMF to each reaction vessel, followed by the addition of 400 μL of the respective amino acid (3-fold excess), 400 μL 0.5M HOBt and BOP, 300 μL 1M DIEA, the reaction well volume is brought up to 3 mL with DMF, and mixed at 500 rpm for 1 hr. After the second coupling cycle, the reaction block is emptied and the resin-Na-protected peptide is washed with DCM (4.5 mL 4 times).

Na-Boc deprotection is performed by the addition of 4 mL 50% TFA, 2% anisole in DCM and mixed for 5 min at 500 rpms followed by a 20 min deprotection at 20 min. The reaction well is washed with 4.5 mL DCM (4 times), neutralized with 10% DIEA (3 min, 500 rpms, 2 times) followed by a DCM wash (4.5 mL, 2 min, 500 rpms 4 times), and the next coupling cycle is performed as described above. The Fmoc and OFm protecting groups are removed from Dpr and Asp, respectively by treatment with 4.5 mL 25% piperidine in DMF (20 min at 500 rpm) with a positive Kaiser test resulting. The lactam bridge between the Asp and Dpr amino acids is formed using 5-fold excess BOP and 6-fold excess DIEA as coupling agents and mixing at 500 rpms and monitored for cyclization completion by a negative Kaiser test.

Deprotection of the remaining amino acid side chains and cleavage of the amide-peptide from the resin is performed by incubation the peptide-resin with anhydrous hydrogen fluoride (HF, 5 mL, 0° C., 1 hr) and 5% m-cresol, 5% thioanisole as scavengers. After the reaction is complete and the HF has been distilled off, the peptide is ether precipitated (50 mL×1) and washed with 50 mL cold (4° C.) anhydrous ethyl ether. The peptide is filtered off using a coarse grit glass filter, dissolved in glacial acetic acid, frozen and lyophilized. The crude peptide yields ranged from 60% to 90% of the theoretical yields. A 40 mg sample of crude peptide is purified by RP-HPLC using a Shimadzu chromatography system with a photodiode array detector and a semi-preparative reversed phase high performance liquid chromatography (RP-HPLC) $C_{18}$ bonded silica column (Vydac 218TP1010, 1.0×25 cm) and lyophilized. The purified peptide was >95% pure as determined by analytical RP-HPLC and had the correct molecular mass (University of Florida protein core facility).

It is recognized that it is preferable to use a protecting group for any reactive functionality such as a carboxyl, hydroxyl and the like. This is standard practice, well within the normal practice of the skilled artisan.

The indicated steps may be varied to increase yield of desired product. The skilled artisan will recognize the judicious choice of reactants, solvents, and temperatures is an important component in any successful synthesis. Determination of optimal conditions, etc. is routine. Thus the skilled artisan can make a variety of compounds using the guidance of the above general description.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when potentially reactive functionalities on the molecule are masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids with reactive side chains used as starting materials are preferably blocked to prevent undesired side reactions.

Melanocortin Functional Activity and Selectivity

Melanocortin receptor functional activity can be evaluated using various methods known in the art. Examples of such methods are measurement of second messenger responses, in particular cAMP, the use of modified cell systems yielding color reaction upon accumulation of second messenger elements such as cAMP, e.g. as described by Chen et al. (*Anal Biochem.*, 226:349-54 (1995)) and Schild, H. O. (*Brit J Pharmacol.*, 2:189-206 (1947)), Cytosensor Microphysiometer techniques (see Boyfield et al., *Biochem Soc Trans.*; 24(1): 57S (1996)), or the study of physiological effects caused by the ligands of the invention may be applied by using the ligands of the invention alone, or in combination with natural or synthetic melanotropin peptides.

In certain embodiments, the MCPR ligands of the present invention will interact preferentially (i.e., selectively) to MC4R, relative to the other melanocortin receptors. Selectivity is particularly important when the compounds are administered to humans or other animals, to minimize the number of side effects associated with their administration.

Therapeutic Compositions and Administration

Therapeutic compositions of MCPR ligands are within the scope of the present invention. Such compositions may comprise a therapeutically effective amount of a MCPR ligand, or peptides, fragments, variants, derivatives, or pharmaceutically acceptable salts thereof, in admixture with a pharmaceutically acceptable carrier. Optionally, the MCPR ligand may be formulated in an acid-salt form. The carrier material may be water for injection, preferably supplemented with other materials common in solutions for administration to mammals such as, for example, alumina, lecithin, d-α-tocopherol, polyethyleneglycol, surfactants, serum proteins such as human serum albumin, phosphates, glycine, sorbic acid, and potassium sorbate.

Typically, a MCPR ligand therapeutic compound will be administered in the form of a composition comprising a purified ligand, or peptide, fragment, variant, or derivative thereof, optionally in its pharmaceutically acceptable salt form, in conjunction with one or more physiologically acceptable carriers, excipients, or diluents.

Pharmaceutically acceptable salts of for the MCPR ligands of the present invention include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycolate, hemisulfate, hydrochloride, hydrobromide, hydroiodide, lactate, maleate, malonate, methanesulfonate, nicotinate, nitrate, oxalate, pectinate, phosphate, salicylate, succinate, sulfate, tartrate, thiocyanate, and other such pharmaceutically acceptable salts.

Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

Any MCPR ligand composition of the invention can be administered parenterally. Alternatively, such compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of MCPR ligand compositions useful for practicing the present invention may be prepared for storage by mixing the selected composition having the desired degree of purity with optional physiologically acceptable carriers, excipients, or stabilizers (*Remington's Pharmaceutical Sciences*, 18$^{th}$ Edition, A. R. Gennaro, ed., Mack Publishing Company (1990)) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids;

antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of the MCPR ligand composition(s) of the present invention to be employed therapeutically will depend, for example, upon the therapeutic objectives such as the indication for which the MCPR ligand is being used, the route of administration, and the condition of the patient. Accordingly, it will be necessary for the therapist to titer the dosage and modify the route of administration as required to obtain the optimal therapeutic effect. A typical daily dosage may range from about 0.01 mg/kg to up to 1000 mg/kg or more, depending on the factors mentioned above. Typically, a clinician will administer the composition until a dosage is reached that achieves the desired effect. The composition may therefore be administered as a single dose, or as two or more doses (which may or may not contain the same amount of the peptide) over time, or as a continuous infusion via implantation device or catheter.

The peptide compositions of the subject invention to be used for in vivo administration must be sterile. This is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accordance with known methods, i.e., oral, injection or infusion by intravenous, intraperitoneal, intracerebral (intraparenchymal), intracerebroventricular, intramuscular, intraocular, intraarterial, or intralesional routes, intranasal, or by sustained release systems or implantation device which may optionally involve the use of a catheter. Where desired, the compositions may be administered continuously by infusion, bolus injection or by implantation device.

Alternatively or additionally, the composition may be administered locally via implantation into the selected area using a membrane, sponge, or other appropriate material onto which a peptide of the subject invention has been absorbed.

Where an implantation device is used, the device may be implanted into any suitable tissue or organ, and delivery of MCPR ligands may be performed directly through the device via bolus, or via continuous administration, or via catheter using continuous infusion.

According to the present invention, MCPR ligands may be administered in a sustained release formulation or preparation. Suitable examples of sustained-release preparations include semipermeable polymer matrices in the form of shaped articles, i.e., films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers*, 22:547-556 (1983)), poly(2-hydroxyethyl-methacrylate) (Langer et al., *J. Biomed. Mater. Res.*, 15:167-277. (1981) and Langer, *Chem. Tech.*, 12:98-105 (1982)), ethylene vinyl acetate (Langer et al., supra) or poly-D(-)-3-hydroxybutyric acid (EP 133,988). Sustained-release compositions also may include liposomes, which can be prepared by any of several methods known in the art (i.e., Eppstein et al., *Proc. Natl. Acad. Sci. USA,* 82:3688-3692 (1985); EP 36,676; EP 88,046; EP 143,949).

The MCPR ligands of the invention, or fragments, variants, and derivatives thereof, may be employed alone, together, or in combination with other pharmaceutical compositions. The peptides, fragments, variants, and derivatives of the subject invention may be used in combination with cytokines, hormones, growth factors, antibiotics, anti-inflammatories, and/or chemotherapeutic agents as is appropriate for the indication being treated.

Methods used for membrane encapsulation of cells are familiar to the skilled artisan, and preparation of encapsulated cells and their implantation in patients may be accomplished without undue experimentation. See, i.e., U.S. Pat. Nos. 4,892,538; 5,011,472; and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described, for example, in U.S. Pat. No. 5,653,975 (Baetge et al., CytoTherapeutics, Inc.). The cells, with or without encapsulation, may be implanted into suitable body tissues or organs of the patient.

As discussed above, it may be desirable to treat isolated cell populations such as, for example, brain cells and/or neurons with one or more peptides, variants, derivatives and/or fragments of the subject invention. This can be accomplished by exposing the isolated cells to the AGRP/ASP peptide, variant, derivative, or fragment directly, where it is in a form that is permeable to the cell membrane.

The following example illustrates a procedure for practicing the invention. This example should not be construed as limiting the scope of the invention in any way. All percentages are by weight and all solvent mixture proportions are by volume unless otherwise noted.

Example 1

Synthesis and Analysis of AMW3-130 (SEQ ID NO:12)

Materials and Methods

Peptides used in this study were purchased from commercial sources, α-MSH, ACTH(1-24), β-MSH, $γ_2$-MSH (Bachem), and hAGRP(87-132) (Peptides International).

hMC4R In Vitro Receptor Mutagenesis

The human wild type N-terminal Flag tagged hMC4R cDNA was generously provided by Dr. Robert Mackenzie (Ho, G. and MacKenzie, R. G., *J. Biol. Chem.*, 274:35819-35822 (1999)), and was subcloned into the pBluescript plasmid (Stratagene) for subsequent mutagenesis. In vitro hMC4 receptor mutagenesis was performed as described previously (Haskell-Luevano, et al., *Biochemistry*, 40(20):6164-6179 (2001)). Amino acid modifications of the hMC4R were introduced by applying a polymerase chain reaction (PCR) strategy using pfu turbo polymerase (Stratagene) and a complementary set of primers containing the nucleotide mutations(s) resulting in the desired residue change.

After completion of the PCR reaction (95° C. for 30 seconds, 12 cycles of 95° C. for 30 seconds, 55° C. for 1 minute, 68° C. for 9 minutes) the product was purified (Qiaquick PCR Purification Kit, Qiagen) and eluted in water. Subsequently, the sample was cut with Dpn1 (Invitrogen) to linearize the wild type template DNA, leaving only nicked circularized mutant DNA. The mutant hMC4R DNA was then transformed into competent DH5α E. coli cells. Single colonies were selected and the presence of the desired mutant was verified by DNA sequencing. The DNA containing the mutant was then excised and subcloned into the HindIII/XbaI restrictions sites of the pCDNA$_3$ expression vector (Invitrogen). Complete Flag-hMC4R sequences were confirmed free of PCR nucleotide base errors by DNA sequencing (University of Florida sequencing core facilities).

Generation of Stable Cell Lines

Human Embryonic Kidney-293 (HEK-293) cells were maintained as described previously (Haskell-Luevano et al., *Biochemistry*, 40(20):6164-6179 (2001)) in Dulbecco's modified Eagle's medium (DMEM) with 10% fetal calf serum and seeded 1 day prior to transfection at $1 \times 10^6$ cells/100-mm dish. Wild type and mutant DNA in the pCDNA$_3$ expression vector (20 µg) were transfected using the calcium phosphate method (Chen, W. et al., *Anal. Biochem.* 226:349-354 (1995)). Stable receptor populations were generated using G418 selection (0.7-1 mg/ml) for subsequent bioassay analysis.

cAMP Based Functional Bioassay

HEK-293 cells stably expressing wild type and mutant receptors were transfected with 4 µg of cAMP response element (CRE)/β-galactosidase reporter gene as previously described (Haskell-Luevano et al., *Biochemistry*, 40(20):6164-6179 (2001); Chen, W. et al., *Anal. Biochem.* 226:349-354 (1995)). Briefly, 5000-15000 post-transfection cells were plated into collagen treated 96-well plates and incubated overnight. Forty-eight hours post-transfection, the cells were stimulated with 100 µL of peptide ($10^{-6}$-$10^{-12}$M) for α-MSH, ACTH (1-24), and AMW3-130, and 100 µl of peptide ($10^{-5}$-$10^{-11}$M) for γ$_2$-MSH, and β-MSH or forskolin ($10^{-4}$ M) control in assay medium (DMEM containing 0.1 mg/mL BSA and 0.1 mM isobutylmethylxanthine) for 6 h.

The assay media was aspirated and 50 µL of lysis buffer (250 mM Tris-HCL, pH 8.0 and 0.1% Triton X-100) was added. The plates were stored at −80° C. overnight. The plates containing the cell lysates were thawed the following day. Aliquots of 10 µL were taken from each well and transferred to another 96 well plate for relative protein determination. To the cell lysate plates, 40 µL of phosphate-buffered saline with 0.5% BSA was added to each well. Subsequently, 150 µL of substrate buffer [60 mM sodium phosphate, 1 mM MgCl$_2$, 10 mM KCl, 5 mM β-mercaptoethanol, 2 mg/mL of o-Nitrophenyl-β-D-galactopyranoside (ONPG)] was added to each well and the plates were incubated at 37° C. The sample absorbance, OD$_{405}$, was measured using a 96-well plate reader (Molecular Devices).

The relative protein was determined by adding 200 µL 1:5 dilution Bio-Rad G250 protein dye:water to the 10 µL cell lysate sample taken previously, and the OD$_{595}$ was measured on a 96 well plate reader (Molecular Devices). Data points were normalized both to the relative protein content and non-receptor dependent forskolin values. Assays were performed using duplicate data points and repeated in at least three independent experiments. Data analysis, EC$_{50}$, pA$_2$ estimates, and their associated standard errors of the mean, were determined by fitting the data to a nonlinear least-squares analysis using the PRISM program (v4.0), GraphPad Inc.). The antagonistic and inverse agonist properties of hAGRP (87-132) were determined by the ability of this ligand to competitively displace the MTII agonist in a dose-dependent manner. The pA$_2$ values were generated using the Schild analysis method (Schild, H. O., *Brit. J. Pharmacol.* 2:189-206 (1947)). Statistical analysis was performed using a student t-test.

Ligand Synthesis

The chimeric hAGRP-melanocortin ligand AMW3-130 (see Table 1) was synthesized manually using standard Nα 9-fluorenylmethoxycarbonyl (Fmoc) methodology (Carpino, L. A. and Han, G. Y., *J. Org. Chem.*, 37:3404-3409 (1972); Chang, C. and Meienhofer, J., *Int. J. Pept. Protein Res.*, 11:246-249 (1978)).

TABLE 1

Amino acid sequences of endogenous and AMW3-130 chimeric AGRP-melanocortin ligands of this Example

| Name | Amino Acid Sequence |
|---|---|
| α-MSH | Ac-Ser-Tyr-Met-Glu-His-Phe-Arg-Trp-Gly-Lys-Pro-Val-NH$_2$ (SEQ ID NO: 1) |
| β-MSH | Ala-Glu-Lys-Lys-Asp-Glu-Gly-Pro-Tyr-Arg-Met-Glu-His-Phe-Arg-Trp-Gly-Ser-Pro-Pro-Lys-Asp (SEQ ID NO: 2) |
| γ-MSH | Tyr-Val-Met-Gly-His-Phe-Arg-Trp-Asp-Arg-Phe-Gly (SEQ ID NO: 3) |
| ACTH (1-24) | Ser-Tyr-Ser-Met-Glu-His-Phe-Arg-Trp-Gly-Lys-Pro-Val-Gly-Lys-Lys-Arg-Arg-Pro-Val-Lys-Tyr-Pro-Asn (SEQ ID NO: 4) |
| AMW3-130 | Tyr-c[Cys-His-DPhe-Arg-Trp-Asn-Ala-Phe-Cys]-Tyr-NH$_2$ (SEQ ID NO: 12) |

The AMW3-130 ligand was assembled on O-fluorenylmethoxycarbonyl-Rink Amide Resin (0.40 meq/g substitution) purchased from Peptides International (Louisville, Ky.). The synthesis (0.26 mmol scale) was performed using a manual synthesis reaction vessel. Each synthetic cycle consisted of the following steps: (i) removal of the Nα Fmoc group by 20% piperidine in DMF (1×2 min, 1×20 min) (ii) single 2 h coupling of Fmoc-amino acid (3 eq) using BOP (3 eq), HOBt (3 eq) and DIEA (6 eq) in DMF and repeated until the ligand synthesis was complete.

The presence or absence of the Nα free amino group was monitored using the Kaiser Test (Kaiser, E. et al., *Anal. Biochem.*, 34:595-598 (1970)). After the completed synthesis, the ligands were cleaved from the resin and deprotected using a cleavage cocktail consisting of 82.5% TFA, 5% H$_2$O, 5% EDT, 5% phenol and 2.5% TIS for 3 hours at room temperature. After cleavage and side chain deprotection the solution was concentrated and the ligand was precipitated and washed using cold (40° C.), anhydrous diethyl ether.

The crude linear ligand was purified by reversed-phase HPLC using Shimadzu chromatography system with a photodiode array detector and a semi-preparative RP-HPLC C18 bonded silica column (Vydac 218tp1010, 1.0×25 cm). The purified linear ligand was oxidized to the disulfide form by reaction with 5% DMSO in $H_2O$. The peptide was dissolved at a concentration of 0.37 mg/mL and the solution was allowed to react at 20° C. The oxidation process was monitored using analytical RP-HPLC for the disappearance of the linear ligand and formation of the cyclized product.

The purified ligands were at least >98% pure as determined by RP-HPLC in two diverse solvent systems and had the correct molecular mass of 1508.0 (University of Florida Protein Core Facility). HPLC k'=[(ligand retention time−solvent retention time)/solvent retention time] in solvent system 1 (k'=5.7 in 10% acetonitrile in 0.1% trifluoracetic acid/water and a gradient to 90% acetonitrile over 35 min) or solvent system 2 (k'=9.9 in 10% methanol in 0.1% trifluoracetic acid/water and a gradient to 90% methanol over 35 min). An analytical Vydac $C_{18}$ column (Vydac 218TP104) was used with a flow rate of 15 mL/min. The percentage ligand purity is determined by HPLC at a wavelength of 214λ.

Results

Discovery and characterization of human MC4R polymorphisms has become an area of research attempting to understand the genetics of energy homeostasis in obese humans. In this Example, eleven hMC4R polymorphisms were pharmacologically characterized in vitro, using stably transfected HEK-293 cells, for their ability to be stimulated by the endogenous melanocortin agonists α-MSH, β-MSH, γ$_2$-MSH, ACTH(1024) (see Table 2), as well as the modified endogenous melanocortin receptor antagonist hAGRP(87-132) (see Table 3).

In this Example, eleven human MC4R polymorphisms were pharmacologically characterized (FIG. 1). The eleven human MC4R polymorphisms were analyzed to assess biofunction and interaction with various endogenous melanocortin receptor agonists and a ligand of the invention, AMW3-130 (SEQ ID NO:12). Analysis results indicated that these human MC4R polymorphisms caused a significant decrease in endogenous melanocortin receptor agonist potency, and reported the discovery that the synthetic ligand AMW3-130 can "rescue" agonist function at these hMC4Rs.

TABLE 3

Summary of the polymorphic nMC4R pharmacology of the endogenous C-terminal antagonist agouti-related protein ligand [hAGRP(87-132)].

| Mutation | Antagonist pA2 hAGRP(87-132) |
|---|---|
| WT# | 8.28 ± 0.11 |
| S58C | 8.02 ± 0.13 |
| N97D | 7.44 ± 0.11* |
| I102S | 8.17 ± 0.10 |
| L106P | 8.27 ± 0.12 |
| S127L | 7.06 ± 0.16* |
| I137T | 8.33 ± 0.12 |
| T150I | 8.34 ± 0.06 |
| R165Q | 8.57 ± 0.06 |
| R165W | 8.52 ± 0.17 |
| G252S | 8.53 ± 0.02 |
| V253I | 8.41 ± 0.17 |
| C271Y | 8.45 ± 0.03 |
| I301T | 8.60 ± 0.07 |

Indicates the average from greater than nine independent experiments. The antagonistic pA2 values were determined using the Schild analysis and the agonist MTII (Ki = −Log pA2).
The indicated errors for the functional data (pA2) represent the standard error of the mean determined from at least three independent experiments.
*p < 0.05.

TABLE 2

Human MC4R Polymorphisms that respond differently to the endogenous melanocortin receptor agonists but possess nM agonist potency to AMW3-130.

| Mutation | α-MSH EC50(nM) | β-MSH EC50(nM) | γ2-MSH EC50(nM) | ACTH(1-24) EC50(nM) | AMW3-130 EC50(nM) |
|---|---|---|---|---|---|
| WT# | 0.65 ± 0.19 | 0.42 ± 0.13 | 73 ± 24 | 0.65 ± 0.15 | 0.21 ± 0.08 |
| S58C | 18.5 ± 6.05** | 15.3 ± 6.60* | 2360 ± 960* | 24.4 ± 6.63** | 0.53 ± 0.22 |
| N97D | >10 | 660 ± 47** | >10 | >10 | 4.02 ± 0.38** |
| I102S | 260 ± 58** | 150 ± 52* | 3620 ± 1022* | 480 ± 89** | 0.44 ± 0.05 |
| L106P | 50% at 1 μM | 356 ± 53** | 2660 ± 370* | 40% at 1 μM | 0.62 ± 0.14 |
| S127L | 5.49 ± 0.80** | 2.22 ± 0.88* | 930 ± 170** | 11.4 ± 5.37* | 0.40 ± 0.12 |
| T150I | 8.14 ± 3.2* | 6.53 ± 2.81* | 1300 ± 760* | 14.0 ± 4.87* | 0.90 ± 0.20 |
| R165Q | 18.7 ± 10.8* | 6.31 ± 2.94* | 1070 ± 330* | 39 ± 6.2** | 0.094 ± 0.005 |
| R165W | 21.5 ± 5.54* | 7.91 ± 2.34* | 1140 ± 350* | 58 ± 19.3* | 0.25 ± 0.021 |
| G252S | 6.11 ± 1.75* | 0.53 ± 0.12 | 409 ± 50** | 10.9 ± 3.89* | 0.13 ± 0.02 |
| C271Y | 48% at 1 μM | 154 ± 12** | 58% at 10 μM | 42% at 1 μM | 0.80 ± 0.32 |
| I301T | 8.42 ± 1.64** | 2.44 ± 0.44* | 370 ± 100* | 16 ± 2.63* | 0.13 ± 0.02 |

Indicates the average from greater than nine independent experiments at the wild type (WT) hMC4R. The values indicated represent the mean of at least three independent experiments with the standard error of the mean indicated.
>10 indicates that an EC50 value was not reportable at up to 10 μM ligand concentrations. A percentage value indicates that some stimulatory agonist pharmacology resulted at up to 10 μM concentrations, but the maximal stimulation levels were less then the non-receptor dependent forskolin control level.
Statistical analysis was performed using a student T-test compared to the wild type receptor values with
*p < 0.05,
**p < 0.01.

FIG. 2 summarizes the agonist pharmacology of eleven hMC4R polymorphic receptors relative to the wild type hMC4R for certain endogenous melanocortin agonists as well as the synthetic AMW3-130 agonist ligand.

The S58C hMC4R was identified as a heterozygous polymorphism in an obese human (Dubern, B. et al., *J. Pediatr.*, 139(2):204-209 (2001)), and resulted in the inability of the endogenous melanocortin agonists α-MSH, γ$_2$-MSH, and ACTH(1-24) to stimulate this receptor at up to $10^{-5}$ M concentrations.

Interestingly, β-MSH was able to stimulate this N97D hMC4R, albeit with 1570-fold decreased agonist potency.

The I102S hMC4R was observed as a heterozygous polymorphism in an obese human (Dubern, B. et al., *J. Pediatr.*, 139(2):204-209 (2001)), and resulted in 50- to 738-fold decreased agonist potency.

The L106P hMC4R was also observed as a heterozygous polymorphism in an obese human (Yeo, G. S. et al., *Hum. Mol. Genet.*, 12(5):561-574 (2003)) and resulted only in 40% to 50% stimulation by α-MSH and ACTH(1-24) at up to one μM concentrations with 36-fold decreased $\gamma_2$-MSH potency and 609-fold decreased β-MSH potency.

The S127L hMC4R was observed in an obese patients as a heterozygous polymorphism (Lubrano-Berthelier, C. et al., *Hum. Mol. Genet.*, 12(2):145-153 (2003); and Hinney, A. et al., *J. Clin. Endocrinol. Metab.*, 88(9):4258-4567 (2003)), and only possessed 5- to 18-fold decreased endogenous melanocortin agonist potency.

The T150I hMC4R, observed as a heterozygous polymorphism in an obese human (Vaisse, C. et al., *J. Clin. Invest.*, 106(2):253-262 (2000)), possessed 13- to 22-fold decreased agonist potency.

The R165Q (Yeo, G. S. et al., *Hum. Mol. Genet.*, 12(5):561-574 (2003); Larsen, L. H. et al., *J. Clin. Endocrinol. Metab.*, 90(1): 219-224 (2005); and Farooqi, I. S. et al., *J. Clin. Invest.*, 106(2):271-279 (2000)) and R165W (Yeo, G. S. et al., *Hum. Mol. Genet.*, 12(5):561-574 (2003); Hinney, A. et al., *J. Clin. Endocrinol. Metab.*, 88(9):4258-4567 (2003); Hinney, A. et al., *J. Clin. Endocrinol. Metab.*, 84(4):1483-1486 (1999); and Branson, R. et al., *N. Engl. J. Med.*, 348 (12):1096-1103 (2003)) hMC4R5, observed as a heterozygous polymorphism in an obese humans, resulted in 15 to 90-fold decreased agonist potency of the endogenous melanocortin agonists.

The G252S hMC4R, observed as a heterozygous polymorphism in obese humans (Hinney, A. et al., *J. Clin. Endocrinol. Metab.*, 88(9):4258-4567 (2003); and Hinney, A. et al., *J. Clin. Endocrinol. Metab.*, 84(4):1483-1486 (1999)), resulted in equipotent β-MSH potency, as compared to the wild type hMC4R, but possessed 6- to 17-fold decreased α-MSH, $\gamma_2$-MSH, and ACTH(1-24) agonist potency.

The C271Y hMC4R, also observed as a heterozygous polymorphism in obese humans (Yeo, G. S. et al., *Hum. Mol. Genet.*, 12(5):561-574 (2003); and Farooqi, I. S. et al., *J. Clin. Invest.*, 106(2):271-279 (2000)), was only stimulated to 42% to 58% maximal stimulation at 1 μM concentrations of α-MSH, $\gamma_2$-MSH, and ACTH(1-24), while β-MSH was able to stimulate a maximal response, albeit with 367-fold decrease agonist potency.

Finally, the I301T hMC4R, a heterozygous polymorphism in an obese human (Vaisse, C. et al., *J. Clin. Invest.*, 106(2): 253-262 (2000)), possessed 5- to 25-fold reduced endogenous melanocortin agonist potency.

Interestingly, AMW3-130 (SEQ ID NO:12) possessed equipotent activity at the S58C, I102S, L106P, I137T, T150I, R165Q, R165W, G252S, V253I, C271Y, and I301T polymorphic hMC4Rs, relative to the wild type control (see Table 3), while the N97D and S127L hMC4Rs resulted in statistically significant decreased hAGRP(87-132) antagonist potency. At all these polymorphic hMC4Rs, the synthetic AGRP-melanocortin chimeric ligand AMW3-130 (see Table 1) possessed sub nM to mM agonist $EC_{50}$ potency (see Table 2, and FIG. 2).

The chimeric AGRP-melanocortin agonist ligand AMW3-130 was designed based upon the hypothesis that the antagonist hAGRP(111-113) Arg-Phe-Phe residues were mimicking the endogenous melanocortin agonist Phe-Arg-Trp (7-9 amino acids, based upon a-MSH numbering) interactions with the MC4R (Wilczynski, A. et al., *J. Med. Chem.*, 47(9): 2194-2207 (2004)). Subsequent studies using analogues possessing an amide lactam cyclization between a modified Asp (βAsp) and a Lys derivative (diaminopropionic acid Dpr) instead of a disulfide bridge (AMW632) (Wilczynski, A. et al., *J. Med. Chem.*, 48(8):3060-3075 (2005); and disclosed in U.S. patent application Ser. No. 10/602,394) demonstrated that the chimeric AGRP-melanocortin agonist template possessed melanocortin receptor pharmacology distinct from that of either previous reported synthetic melanocortin or AGRP ligands. Thus, these reports demonstrate that the chimeric AGRP-melanocortin ligands of the present invention possess putative ligand-receptor interactions more unique than previously reported derivatives. Further, as demonstrated herein, the ligands of the invention, in particular AMW3-130, can rescue the endogenous melanocortin agonist dysfunction at eleven human MC4R polymorphisms. Moreover, the AMW3-130 ligand provides a novel template that can be developed further as a potential therapeutic agent to treat humans possessing hMC4R polymorphisms.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. An isolated ligand that is biologically active at melanocortin receptors having a sequence selected from the group consisting of SEQ ID NO:12 and SEQ ID NO:68.

2. A composition comprising a ligand having a sequence selected from the group consisting of SEQ ID NO:12 and SEQ ID NO:68, or is a salt thereof.

* * * * *

UNITED STATES PATENT AND TRADEMARK OFFICE
CERTIFICATE OF CORRECTION

| | |
|---|---|
| PATENT NO. | : 8,058,240 B2 |
| APPLICATION NO. | : 12/296446 |
| DATED | : November 15, 2011 |
| INVENTOR(S) | : Carrie Haskell-Luevano |

It is certified that error appears in the above-identified patent and that said Letters Patent is hereby corrected as shown below:

Column 4,
Line 7 "mM to sub" should read --nM to sub--

Column 20,
Line 37, "-Tyr-Met-" should read -- -Tyr-Ser-Met- --

Signed and Sealed this
Thirteenth Day of March, 2012

David J. Kappos
*Director of the United States Patent and Trademark Office*